(12) United States Patent
Joe et al.

(10) Patent No.: US 12,329,368 B2
(45) Date of Patent: Jun. 17, 2025

(54) APPARATUS AND METHOD FOR SEALING A VASCULAR PUNCTURE

(71) Applicant: Access Closure, Inc., Santa Clara, CA (US)

(72) Inventors: Wesley Chung Joe, Fremont, CA (US); Sravanthi Avuthu, Portola Valley, CA (US); Curt D. Guyer, Dublin, CA (US); Richard Repp, San Jose, CA (US); Martin Schnitzer, San Francisco, CA (US)

(73) Assignee: Access Closure, Inc., Santa Clara, CA (US)

( * ) Notice: Subject to any disclaimer, the term of this patent is extended or adjusted under 35 U.S.C. 154(b) by 0 days.

(21) Appl. No.: 18/351,231

(22) Filed: Jul. 12, 2023

(65) Prior Publication Data
US 2024/0090883 A1 Mar. 21, 2024

Related U.S. Application Data

(63) Continuation of application No. 17/445,305, filed on Aug. 17, 2021, now Pat. No. 11,737,740, which is a
(Continued)

(51) Int. Cl.
*A61B 17/00* (2006.01)
*A61B 90/00* (2016.01)

(52) U.S. Cl.
CPC ............... *A61B 17/0057* (2013.01); *A61B 2017/00367* (2013.01); *A61B 2017/00389* (2013.01);
(Continued)

(58) Field of Classification Search
CPC ............ A61B 17/0057; A61B 17/2909; A61B 17/3207; A61B 17/320708;
(Continued)

(56) References Cited

U.S. PATENT DOCUMENTS 4,890,612 A 1/1990 Kensey
6,816,006 B2 11/2004 Cates
(Continued)

FOREIGN PATENT DOCUMENTS

CN 101170949 A 4/2008
CN 101389276 A 3/2009
(Continued)

*Primary Examiner* — Tuan V Nguyen
(74) *Attorney, Agent, or Firm* — ArentFox Schiff LLP

(57) ABSTRACT

Closure devices for sealing a puncture and methods of sealing a puncture are described herein. A closure device may be used to position a sealant in a puncture. The sealant may be provided in a sheath which is retracted to expose the sealant in the puncture. A support member may be advanced to compress the sealant. The device may have a lock that prevents the support member from advancing prematurely. The lock may be unlocked when the sheath is at least partially retracted. The device may have an actuator that controls movement of the sheath and the support member. The lock may remain in a locked position until the sheath is at least partially retracted.

11 Claims, 22 Drawing Sheets

Related U.S. Application Data continuation of application No. 16/257,528, filed on Jan. 25, 2019, now abandoned.

(60) Provisional application No. 62/623,350, filed on Jan. 29, 2018.

(52) U.S. Cl.
CPC ........... *A61B 2017/00623* (2013.01); *A61B 2017/0065* (2013.01); *A61B 2017/00654* (2013.01); *A61B 2017/00893* (2013.01); *A61B 2090/034* (2016.02)

(58) Field of Classification Search
CPC ...... A61B 17/32075; A61B 17/320758; A61B 2017/00623; A61B 2017/0065; A61B 2017/00893; A61B 2017/320716; A61B 2017/320733; A61B 2017/320741; A61B 2017/320766; A61B 2017/320775
See application file for complete search history.

(56) References Cited

U.S. PATENT DOCUMENTS

| | | |
|---|---|---|
| 6,818,008 B1 | 11/2004 | Cates et al. |
| 8,298,259 B2 | 10/2012 | Terwey |
| 8,394,122 B2 | 3/2013 | Bagaoisan et al. |
| 8,568,445 B2 | 10/2013 | Pipenhagen et al. |
| 8,591,542 B2 | 11/2013 | White et al. |
| 8,721,680 B2 | 5/2014 | Hundertmark et al. |
| 8,758,402 B2 | 6/2014 | Jenson et al. |
| 9,131,932 B2 | 9/2015 | Tegels |
| 9,192,364 B2 | 11/2015 | Terwey |
| 9,301,740 B2 | 4/2016 | Thelen et al. |
| 9,713,462 B2 | 7/2017 | Bagaoisan et al. |
| 9,757,105 B2 | 9/2017 | Hundertmark et al. |
| 9,895,144 B2 | 2/2018 | Tegels et al. |
| 2002/0111651 A1 | 8/2002 | Ungs |
| 2003/0060846 A1 | 3/2003 | Egnelov et al. |
| 2005/0267522 A1 | 12/2005 | Yassinzadeh et al. |
| 2005/0274384 A1* | 12/2005 | Tran ................ A61B 17/12031 128/831 |
| 2006/0253037 A1 | 11/2006 | Ginn et al. |
| 2008/0065121 A1 | 3/2008 | Kawaura et al. |
| 2008/0221615 A1 | 9/2008 | Ginn et al. |
| 2012/0089179 A1 | 4/2012 | Ginn et al. |
| 2013/0253579 A1* | 9/2013 | Hundertmark ..... A61B 17/0057 606/214 |
| 2014/0025103 A1 | 1/2014 | Hundertmark et al. |
| 2014/0214075 A1 | 7/2014 | Khosravi et al. |
| 2014/0214076 A1 | 7/2014 | Hundertmark et al. |
| 2015/0342581 A1 | 3/2015 | Mylonakis |
| 2015/0201919 A1 | 7/2015 | Green et al. |
| 2016/0135796 A1 | 5/2016 | Hundertmark et al. |
| 2018/0008246 A1 | 1/2018 | Bagaoisan et al. |
| 2018/0008247 A1 | 1/2018 | Hundertmark et al. |
| 2019/0076638 A1 | 3/2019 | Dailey et al. |

FOREIGN PATENT DOCUMENTS

| | | |
|---|---|---|
| CN | 101897606 A | 12/2010 |
| CN | 107106151 A | 8/2017 |
| CN | 107196151 A | 8/2017 |
| EP | 2064999 A2 | 6/2009 |
| EP | 1893099 B1 | 6/2012 |
| EP | 3745962 A1 | 8/2019 |
| JP | 2012508618 A | 5/2010 |
| JP | 2011508627 A | 3/2011 |
| KR | 1020140138257 A | 12/2014 |
| KR | 1020170083040 A | 7/2017 |
| WO | 2013142515 A1 | 9/2013 |

\* cited by examiner

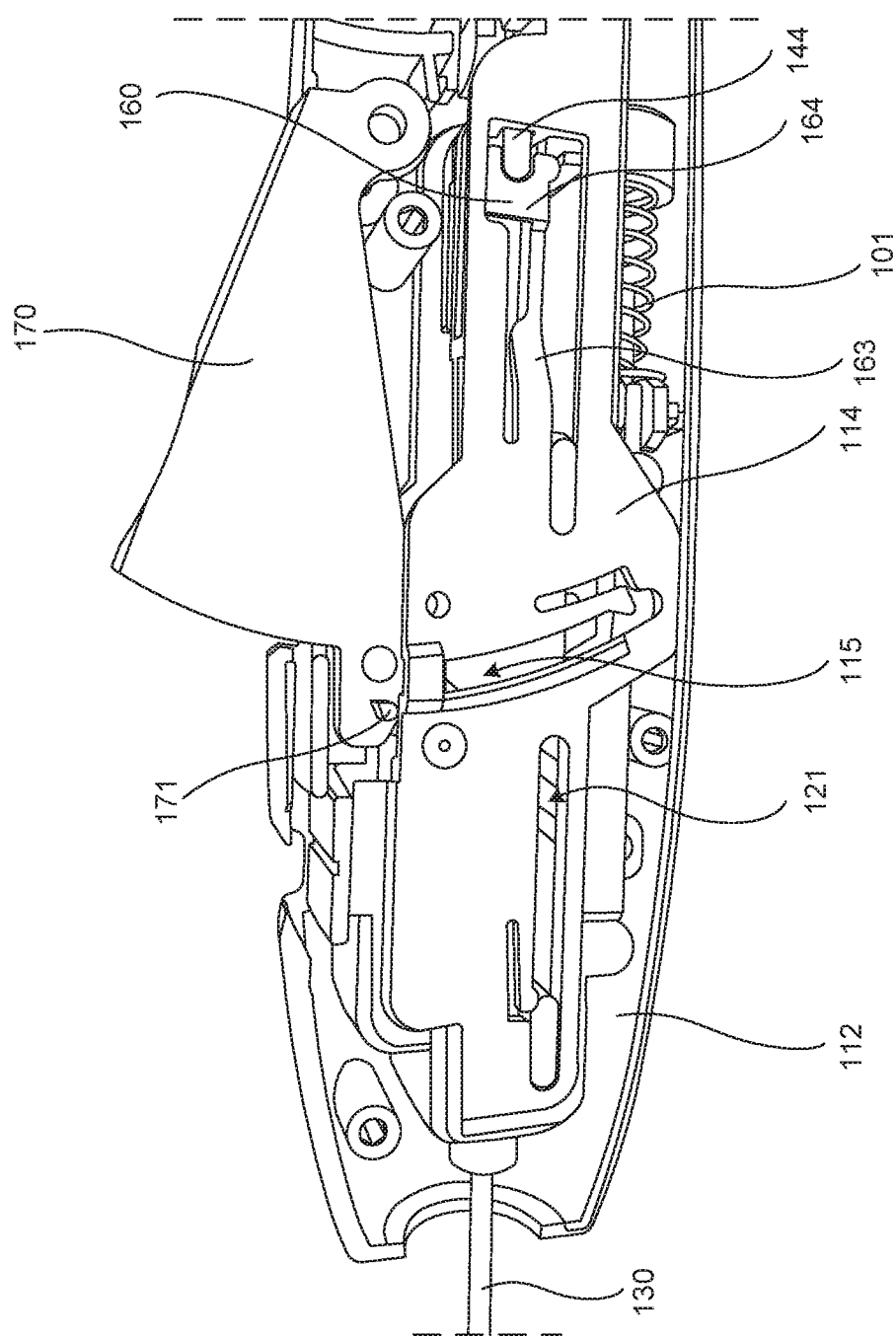

APPARATUS AND METHOD FOR SEALING A VASCULAR PUNCTURE

CROSS-REFERENCE TO RELATED APPLICATIONS

This application is a continuation of U.S. patent application Ser. No. 17/445,305, which was filed on Aug. 17, 2021, which is a continuation of Ser. No. 16/257,528, which was filed on Jan. 25, 2019, and which claims the benefit of U.S. Provisional Patent Application No. 62/623,350, entitled "APPARATUS AND METHOD FOR SEALING A VASCULAR PUNCTURE" and filed on Jan. 29, 2018, which is herein incorporated by reference in its entirety.

FIELD

Devices and methods described herein may be useful for sealing a vascular puncture using a plug or sealant.

BACKGROUND

Some diagnostic or therapeutic procedures require access to a patient's vasculature (e.g., imaging procedure, angioplasty, stent delivery, or otherwise). A puncture through the patient's tissue may be created to access the patient's vasculature percutaneously, i.e., a puncture may be created through the tissue. After completion of the diagnostic or therapeutic procedure, the puncture can be closed by various mechanical or biological solutions, such as by applying external pressure (e.g., manually and/or using sandbags), cinching, suturing, and/or delivering metal implants, plugs, or sealants. However, many of these closure procedures may be time consuming, expensive, and uncomfortable for the patient, requiring the patient to remain immobilized in the operating room, catheter lab, or holding area for extended periods of time. Additionally, some of these prolonged closure procedures may increase the risk of hematoma from bleeding prior to hemostasis.

When closing the puncture using a metal implant, plug, sealant, or other appropriate sealing member, the health care professional may use a vascular closure device to position and deploy the sealing member. The device may include a sheath and a support member. The sealant may be positioned inside a sheath or other protective member. The sheath may be moved proximally to expose the sealant in the puncture. The support member may be moved distally to tamp the sealant. However, tamping the sealant prematurely may cause the sealant to become jammed in the sheath.

SUMMARY

The devices described herein may be used to deploy a sealant in a puncture. These devices may include a sealant sleeve and a support member. During normal operation of the device, the sealant may be initially positioned in a protective member, such as a sealant sleeve. The sealant sleeve may be withdrawn to expose the sealant within the puncture. The support member may be advanced to compress the sealant. It is preferable that at least a portion of the sealant be exposed within the puncture prior to advancing the support member to prevent the sealant from becoming jammed.

The devices described herein may include a handle containing a pull rack and a push rack. The sealant sleeve may extend distally from the pull rack. The support member may be a tube, and may extend distally from the push rack. The pull rack and the push rack may interact with other components of the device to control movement of the sealant sleeve and support member.

The devices described herein may include a releasable lock to prevent premature advancement of the support member, while allowing advancement of the support member after the sealant has been at least partially exposed. It may be beneficial to decouple distal movement of the support member and disengagement of the lock, such that a distal force applied to the support member does not disengage the lock. For example, in some embodiments, proximal movement of the sealant sleeve may release the lock, thereby allowing the support member to move distally.

Another benefit of the devices described herein is their ability to provide a smooth force transition as the lock is disengaged. If the user experiences a sudden increase in force when disengaging the lock, the user may mistakenly believe that they have fully actuated an actuator associated with the sealant sleeve and/or support member, when they may just be experiencing an activation force to disengage the lock from the push rack and/or support member.

Another benefit of the devices described herein is the ability to design the device to expose a desired percentage of the sealant before the lock is released, and continue to control the additional distance and rate that the sleeve retracts as the support member is advanced to tamp the sealant.

Another benefit of the devices described herein is that the support member and push rack may be substantially unbiased relative to the sealant. In other words, the device does not need a spring to bias the push rack distally. Therefore, disengaging the push rack lock does not necessarily cause the push rack to move distally toward the sealant. An actuator may control distal movement of the push rack, which allows the user to have more control over the timing and speed of advancement of the push rack. In addition, the push rack lock may maintain a locked position, even if the push rack is not biased toward the push rack lock.

DESCRIPTION OF THE FIGURES

FIG. 5B is a side view of the device of FIG. 1 in a locating configuration (the sheath adapter and half of the outer housing are not shown).

DETAILED DESCRIPTION

Figure 1:
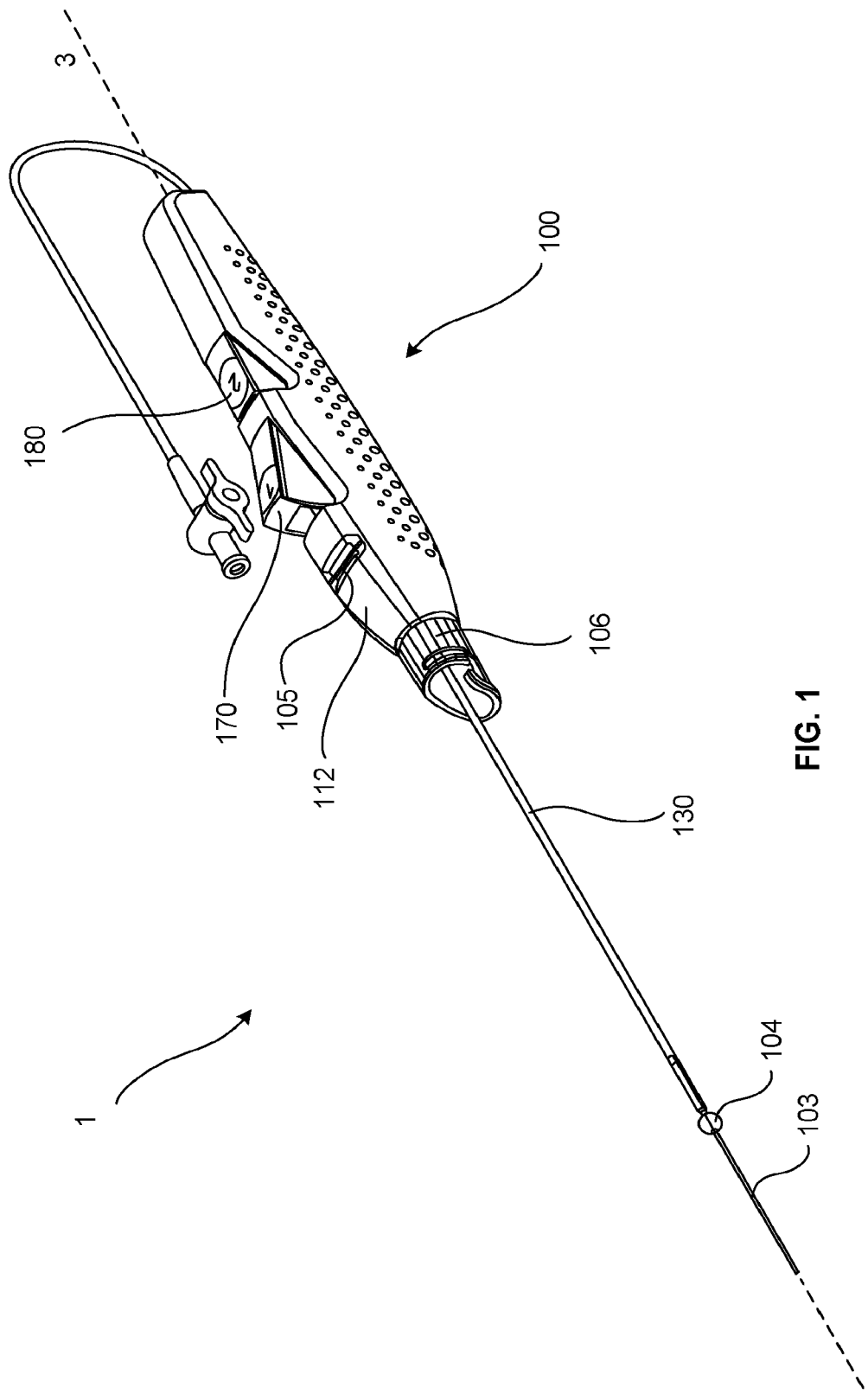
FIG. 1 is a perspective view of a device for delivering a sealant.

A closure system 1 is illustrated in FIGS. 1 and 5A-8C. The closure system 1 may comprise a sealant 2 and a device 100 for delivering the sealant 2. The device 100 may comprise a pull rack 120 and a push rack 140 slidably positioned in an outer housing 112 (also referred to as a handle). The device 100 may also comprise a frame 114 slidably positioned in the outer housing 112. A sealant sleeve 130 may extend distally from the pull rack 120. A support member 150 may extend distally from the push rack 140. The support member 150 may be inserted into the sealant sleeve 130. The sealant 2 may be positioned in the sealant sleeve 130, distal to the support member 150. The device 100 may include a deployment actuator 170 that, when depressed or otherwise actuated, exposes and/or tamps the sealant 2. The device 100 may include a sheath adapter 106 that allows the device to interface with a procedural sheath. The device 100 may include an elongate member 102 and positioning element 104 to position the device 100 before exposing the sealant 2. The device 100 may also include a retraction actuator 180 that retracts the positioning element 104 and the elongate member 102 relative to the support member 150 to withdraw the positioning element 104 and the elongate member 102 through the sealant 2. The device 100 may include various features (described below) to prevent unintended movement of the outer housing 112, deployment actuator 170, retraction actuator 180, pull rack 120, push rack 140, and/or frame 114 relative to one another or relative to other components in the device 100.

Figure 2A:
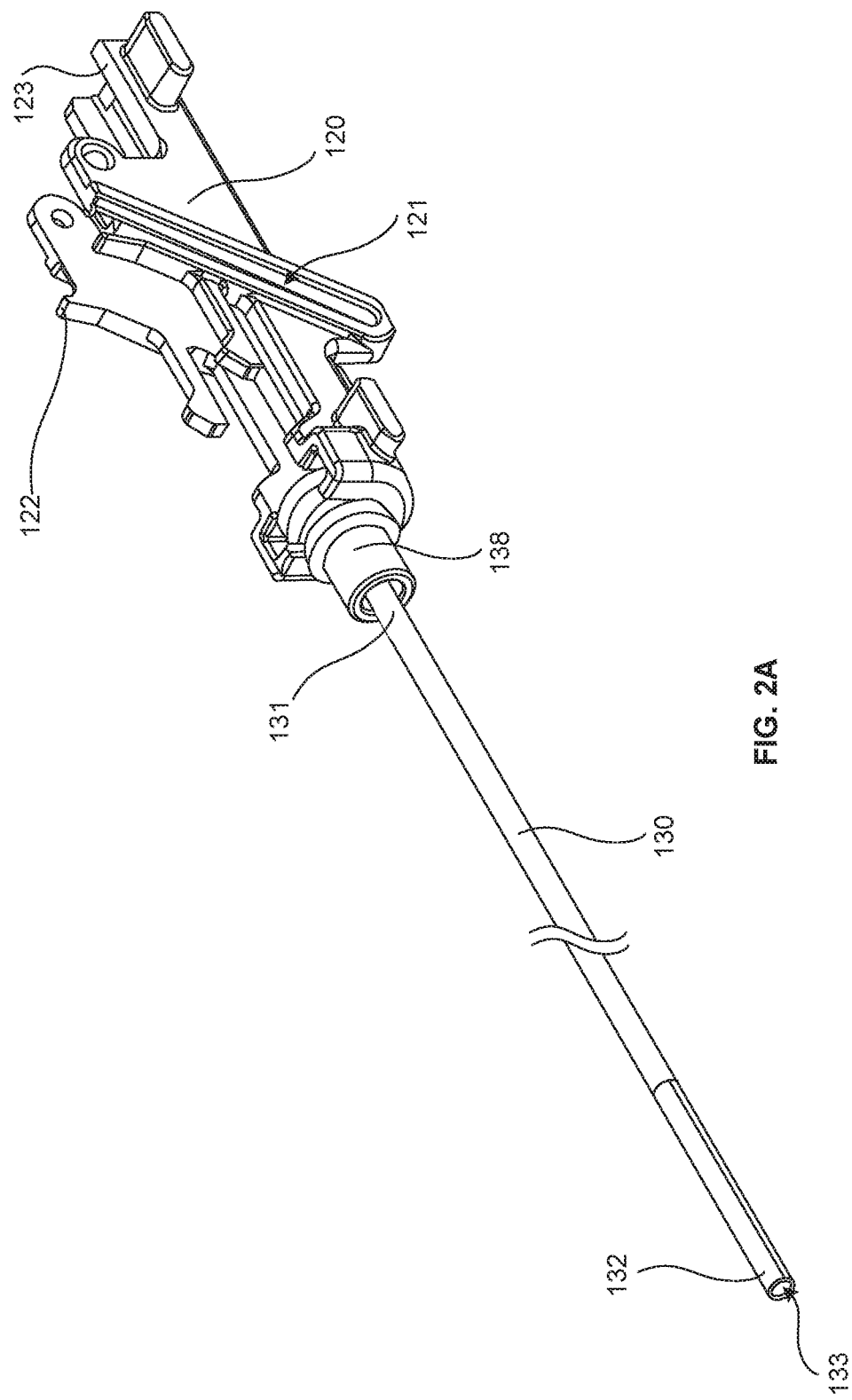
FIG. 2A is a perspective view of a pull rack, sealant sleeve, and connector of the device of FIG. 1.
Figure 2B:
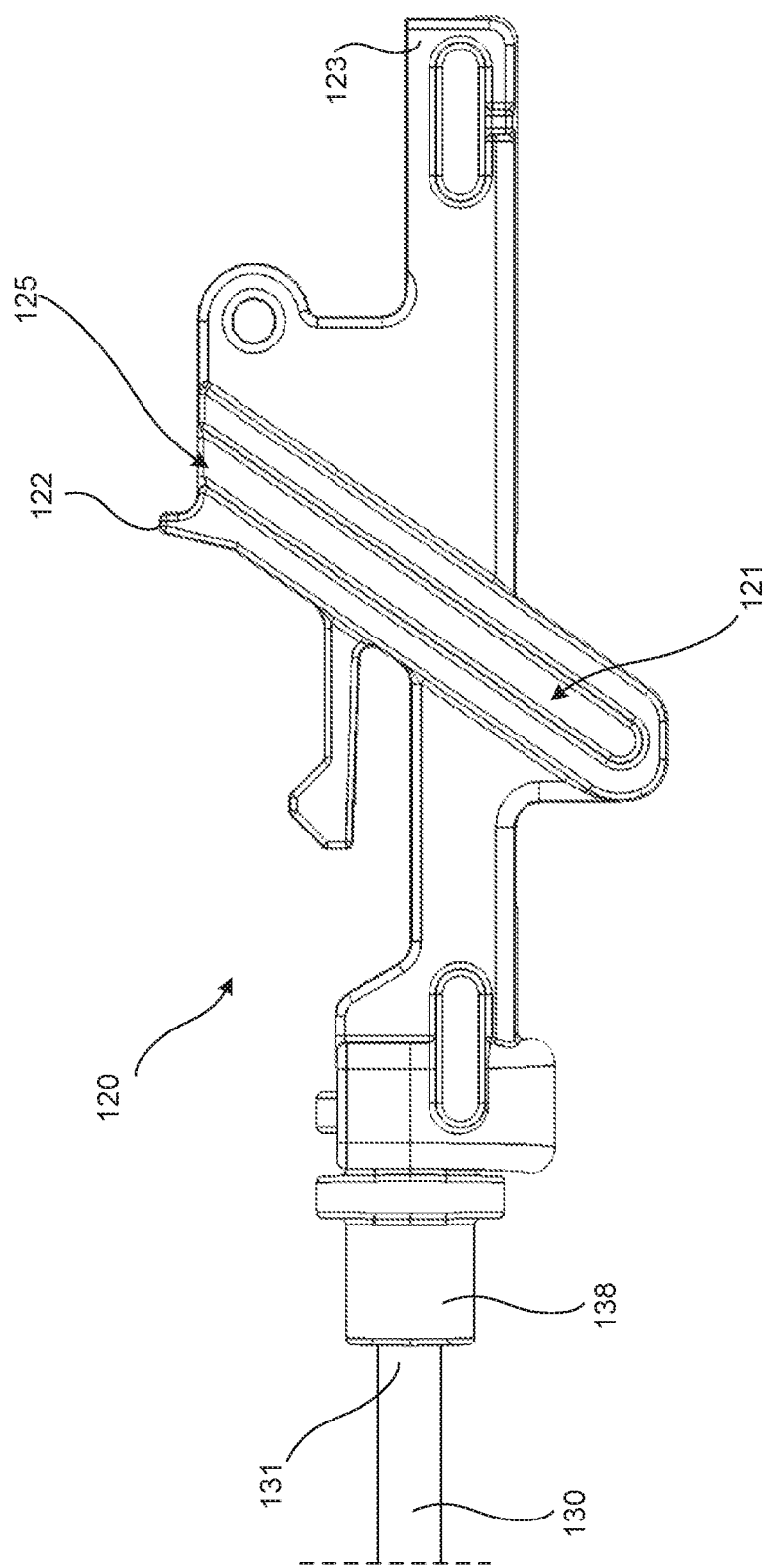
FIG. 2B is a side view of the pull rack, sealant sleeve, and connector of FIG. 2A.

The device 100 may include a pull rack 120 and a sealant sleeve 130, shown in FIGS. 2A-2B. The sealant sleeve 130 may be a tubular member having a proximal section 131, a distal section 132, and a lumen 133. The sealant sleeve 130 may extend along the longitudinal axis 3 of the device 100 as shown in FIG. 1. The sealant 2 may be positioned in the lumen 133 of the sealant sleeve 130, preferably in the distal section 132. The distal section 132 of the sealant sleeve 130 may be rounded or tapered at the distal end to enclose the sealant 2. The proximal section 131 of the sealant sleeve 130 may be coupled to the pull rack 120, such that when the pull rack 120 moves proximally away from the sealant 2, the sealant sleeve 130 also moves proximally, thereby exposing the sealant 2. In one exemplary embodiment, FIGS. 2A-2B show the sealant sleeve 130 indirectly coupled to the pull rack 120 using a connector 138. However, the pull rack 120 and sealant sleeve 130 may be integrally formed, directly coupled, or indirectly coupled using various techniques known in the art. The pull rack 120 may be slidably positioned in the outer housing 112. The pull rack 120 may have an actuating feature 121 (shown as an actuating groove 121 in FIGS. 2A-2B) that is engageable with the deployment actuator 170 (described below) and a push rack lock unlocking feature 123 (shown as a wall 123 protruding from the pull rack 120 in FIGS. 2A-2B) that is engageable with the push rack lock 160 (described below).

Figure 3:
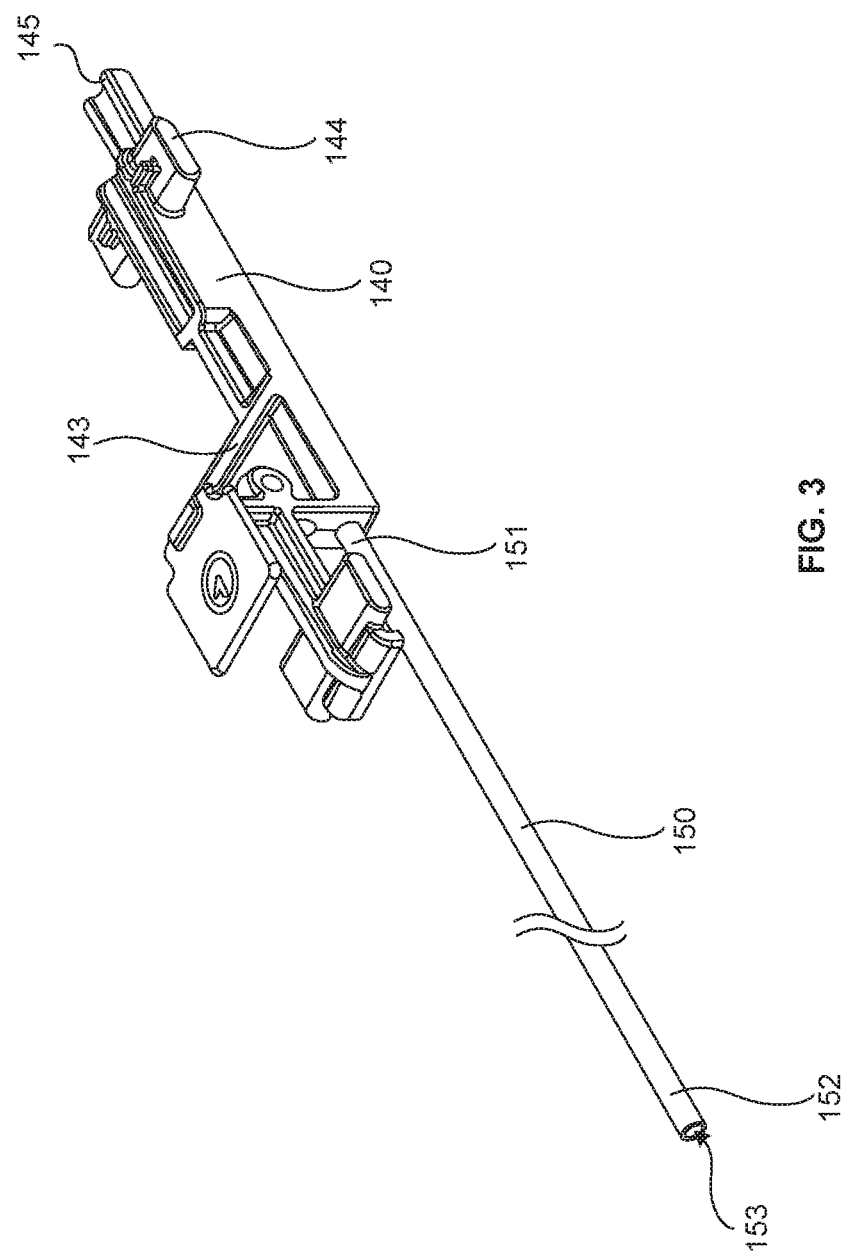
FIG. 3 is a perspective view of a push rack and support member of the device of FIG. 1.

The device 100 may include a push rack 140 and a support member 150, shown in FIG. 3. The support member 150 may be a tubular member (and may be referred to as a tamp tube or tamping member). The support member 150 having a proximal section 151, a distal section 152, and a lumen 153. The support member 150 may extend along the longitudinal axis 3 of the device 100 as shown in FIG. 1. The distal section 152 of the support member 150 may be slidably positioned in the lumen 133 of the sealant sleeve 130, proximal to the sealant 2. The support member 150 may prevent the sealant 2 from moving proximally when the sealant sleeve 130 is withdrawn. The proximal section 151 of the support member 150 may be coupled to the push rack 140, such that when the push rack 140 moves distally toward the sealant 2, the support member 150 also moves distally, thereby tamping or compressing the sealant 2. In an exemplary embodiment, FIG. 3 shows the push rack 140 directly coupled to the support member 150. However, the push rack 140 and support member 150 may be integrally formed, directly coupled, or indirectly coupled using various techniques known in the art. The push rack 140 may be slidably positioned in the outer housing 112. The push rack 140 may have an actuating feature 143 (shown as an actuating ramp 143 in FIG. 3) that is engageable with the deployment actuator 170 and a push rack lock engaging feature 144 (shown as a latch-contacting surface 144 in FIG. 3) that is engageable with the push rack lock 160 (described below). The push rack lock engaging feature 144 may have a distal-facing surface that engages with the push rack lock 160.

Figure 9:
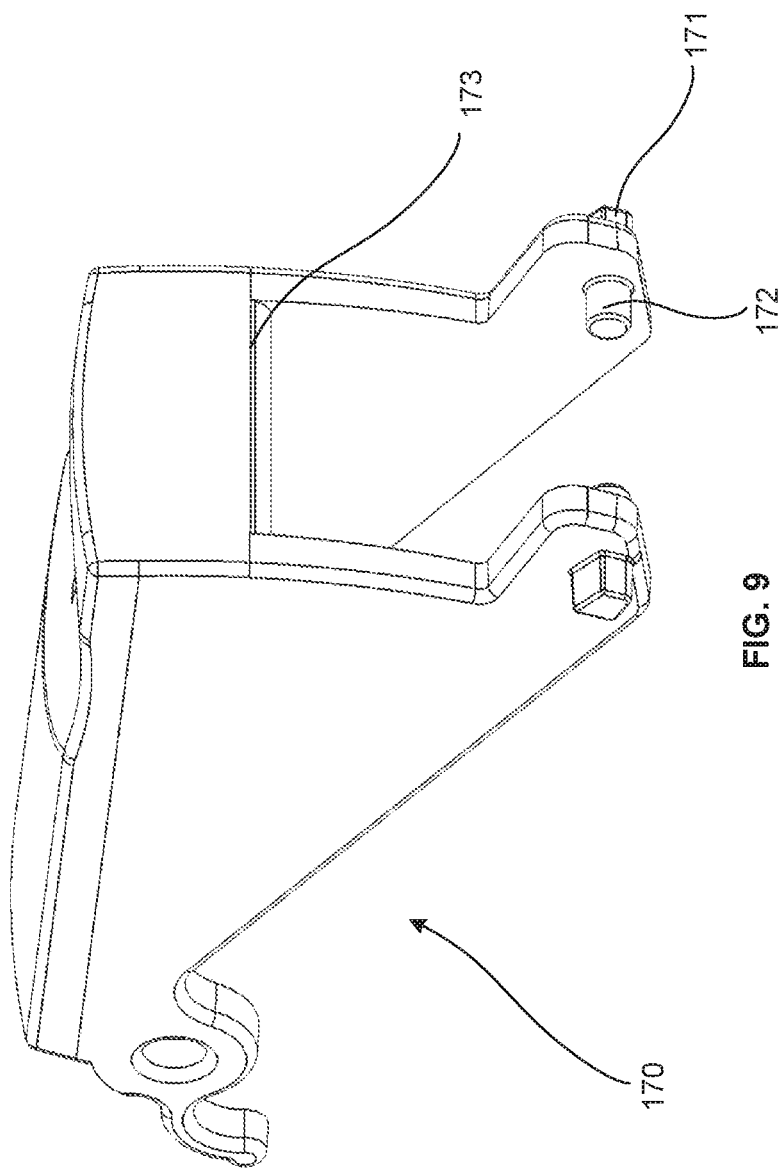
FIG. 9 is a perspective view of a deployment actuator of the device of FIG. 1.

The device 100 may include a deployment actuator 170, shown in FIG. 9. The deployment actuator 170 may be actuatable to move the pull rack 120 (and sealant sleeve 130) proximally and/or move the push rack 140 (and support member 150) distally. The deployment actuator 170 may have a locked position, an unlocked position, a partially actuated position, and a fully actuated position. The deployment actuator 170 may be coupled to the outer housing 112 such that axial movement of the outer housing 112 results in axial movement of the deployment actuator 170. The deployment actuator 170 may be movable relative to the outer housing 112 upon actuation.

Figure 4A:
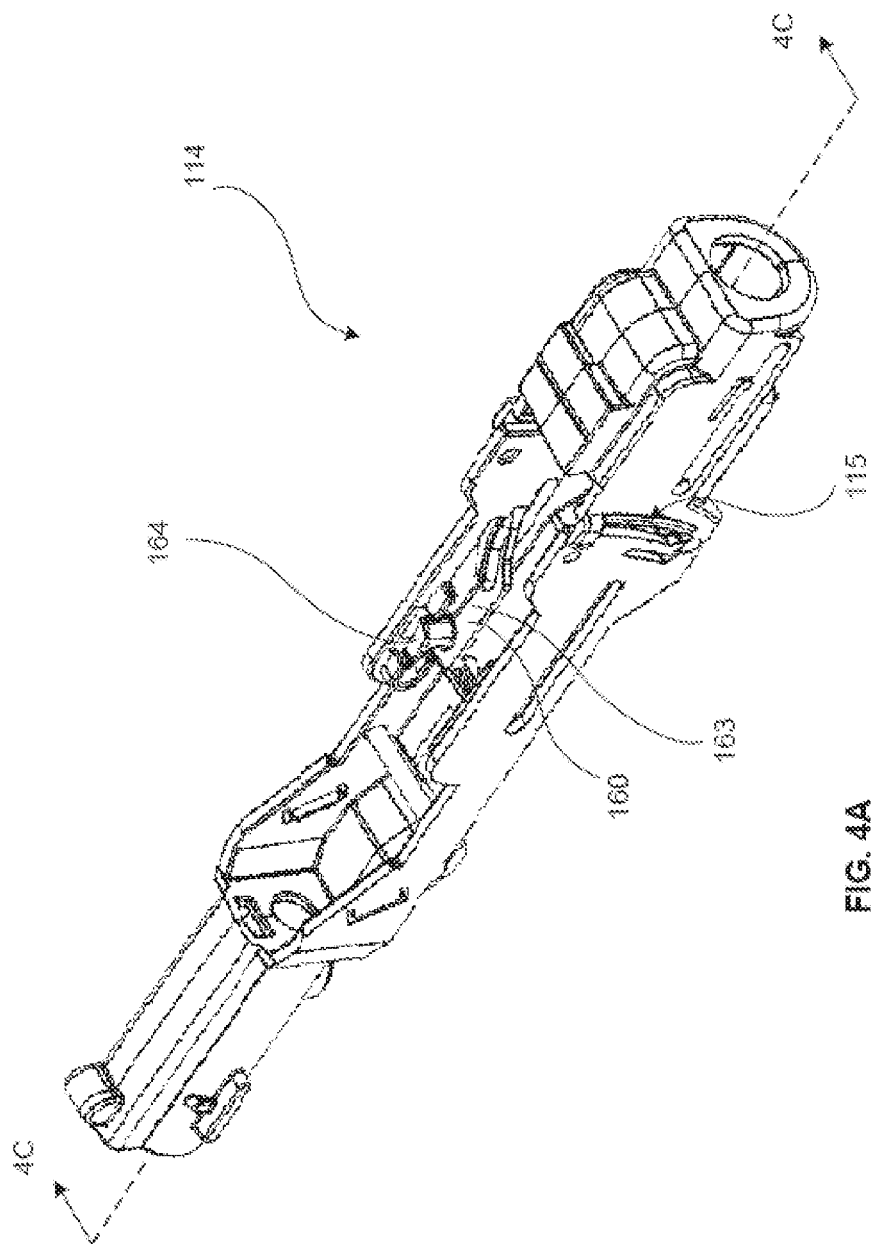
FIG. 4A is a perspective of a frame of the device of FIG. 1.
Figure 4B:
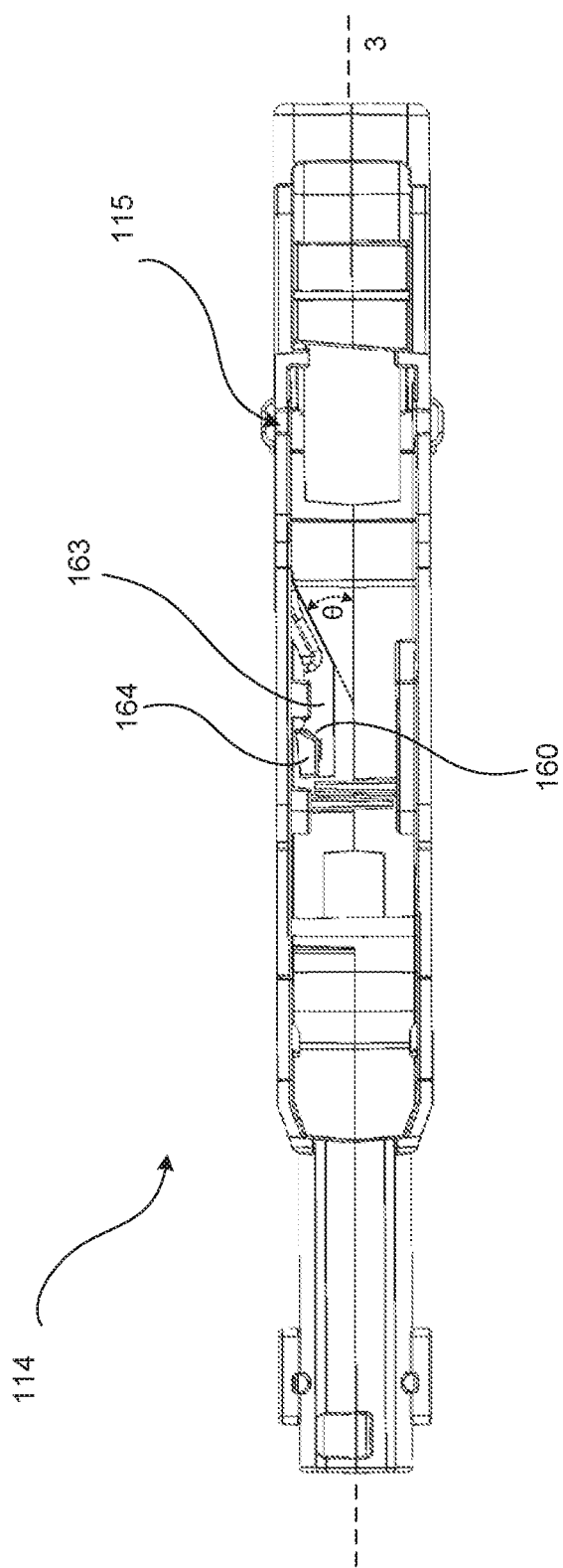
FIG. 4B is a top view of the frame of FIG. 4A.
Figure 4C:
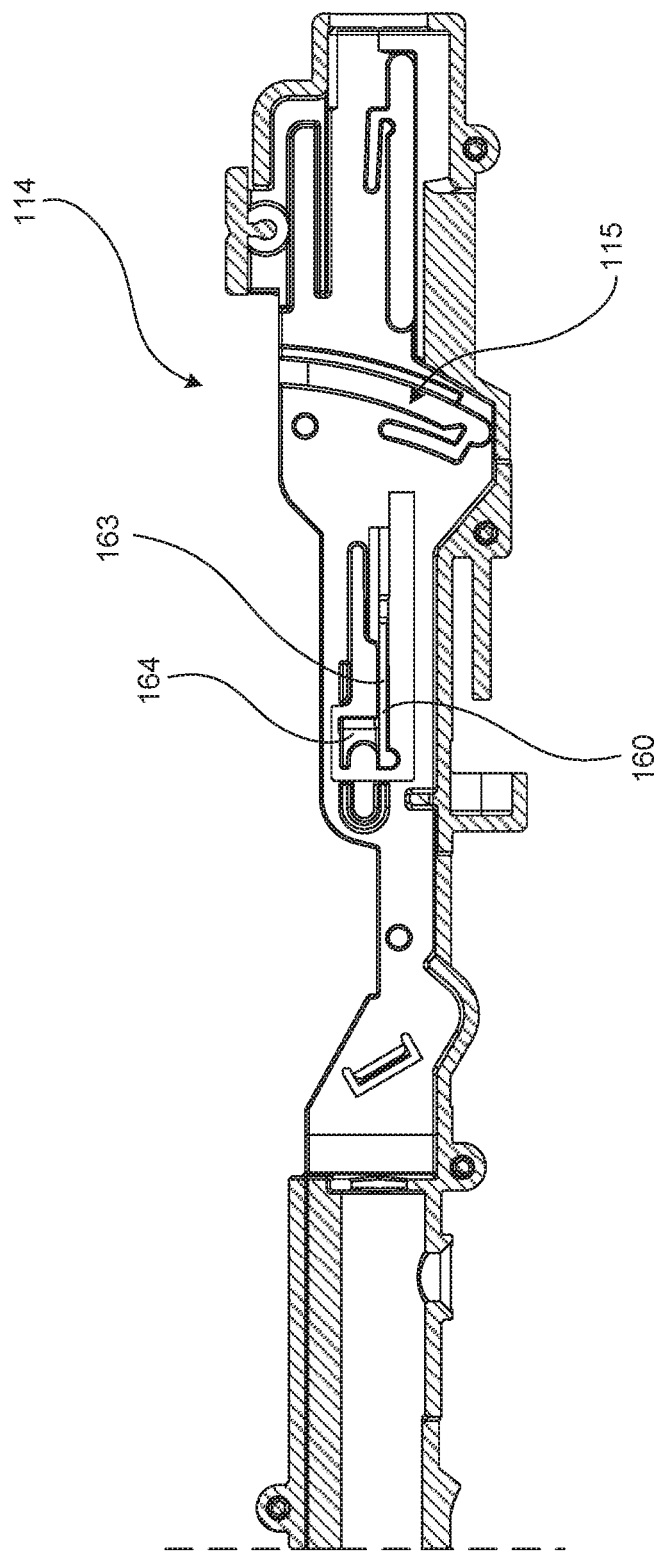
FIG. 4C is a cross-sectional view of the frame of FIG. 4A.

The device 100 may include a frame 114, as shown in FIGS. 4A-4C. The frame 114 (also referred to as an inner frame) may be positioned inside, and axially movable relative to, the outer housing 112. The frame 114 may initially engage the pull rack 120 and push rack 140 such that moving the outer housing 112 proximally relative to the frame 114 also moves outer housing 112 proximally relative to the pull rack 120 and push rack 140. A spring 101, shown in FIG. 5B, may be provided in the device 100 to apply a biasing force that biases the frame 114 proximally relative to the outer housing 112 and the deployment actuator 170, and therefore the spring 101 also applies a biasing force that biases the outer housing 112 and the deployment actuator 170 distally relative to the frame 114. The frame 114 may include a deployment feature 115 (for example, a slot or a groove) which may be engageable with a portion of the deployment actuator 170.

The deployment actuator 170 is shown as a depressible button in FIG. 9, but may alternatively be a slidable button, a lever, a rotating knob, a wheel, or any other actuator that is capable of moving the pull rack 120 proximally and the push rack 140 distally. The deployment actuator 170 may have an actuator locking surface 171 that selectively prevents (or allows) actuation of the deployment actuator 170. In FIG. 9, the actuator locking surface 171 is shown as a pin, but it can be any protrusion or other feature that selectively engages a groove 115 in the frame 114 to selectively allow (or prevent) actuation of the deployment actuator 170. The deployment actuator 170 may have a pull rack actuating surface 172 that drives the pull rack 120 proximally. In FIG. 9, the pull rack actuating surface 172 is shown as a pin that selectively engages a groove 121 in the pull rack 120 to move the pull rack 120 proximally. The deployment actuator 170 may have a push rack actuating surface 173 that drives the push rack 140 distally. In FIG. 9, the push rack actuating surface 173 is shown as a wall that selectively engages the actuating ramp 143 on the push rack 140 to move the push rack 140 distally.

The deployment actuator 170 may be provided in the locked position, shown in FIG. 5B, in which actuation of the deployment actuator 170 is prevented. The deployment actuator 170 may contact the frame 114 to prevent actuation. More specifically, the actuator locking surface 171 may rest on a surface of the frame 114 (in other words, the actuator locking surface 171 may be offset from the groove 115 in the frame 114), thereby preventing the user from actuating the deployment actuator 170. The push rack actuating surface 173 of the deployment actuator 170 may be spaced from the actuating ramp 143 on the push rack.

Figure 6A:
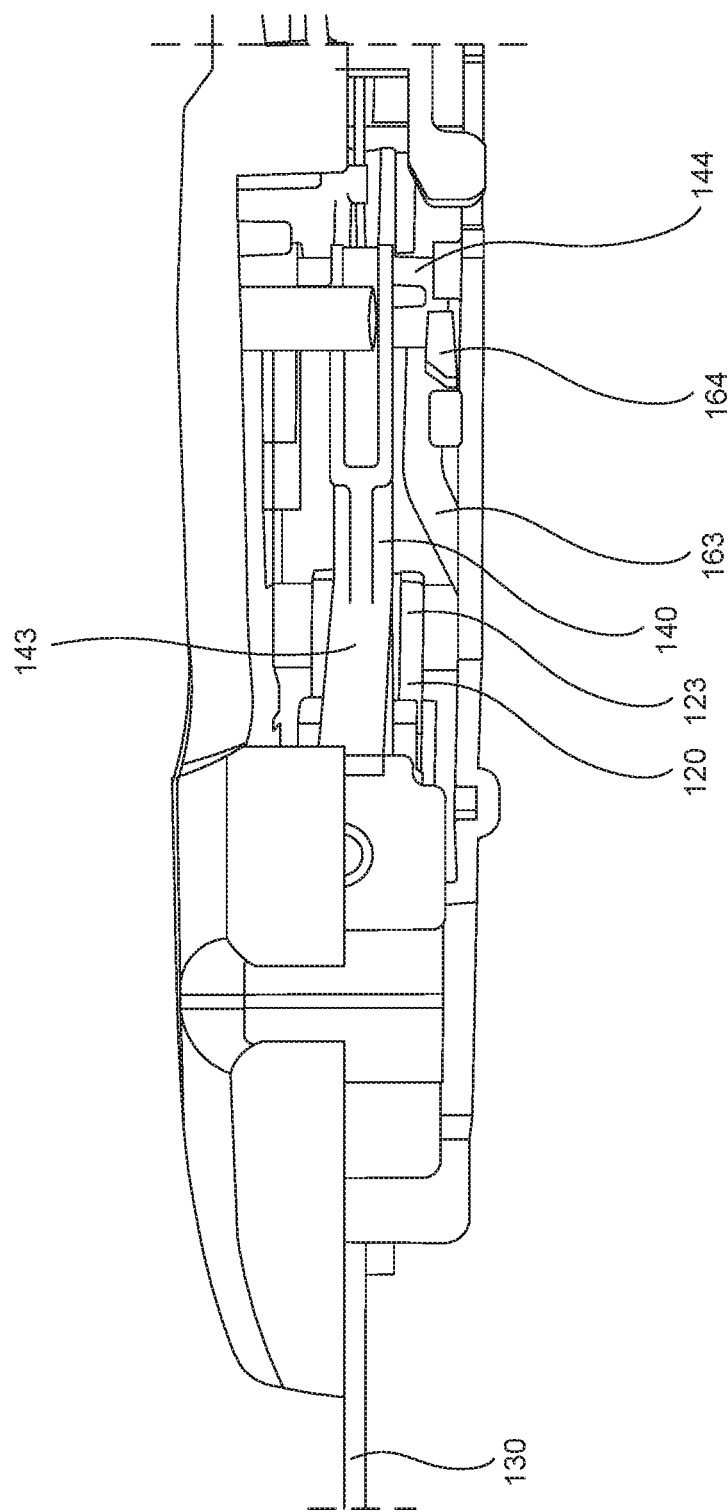
FIG. 6A is a top view of the device of FIG. 1 in a pre-deployment configuration (the deployment actuator, sheath adapter, and half of the outer housing are not shown).
Figure 6B:
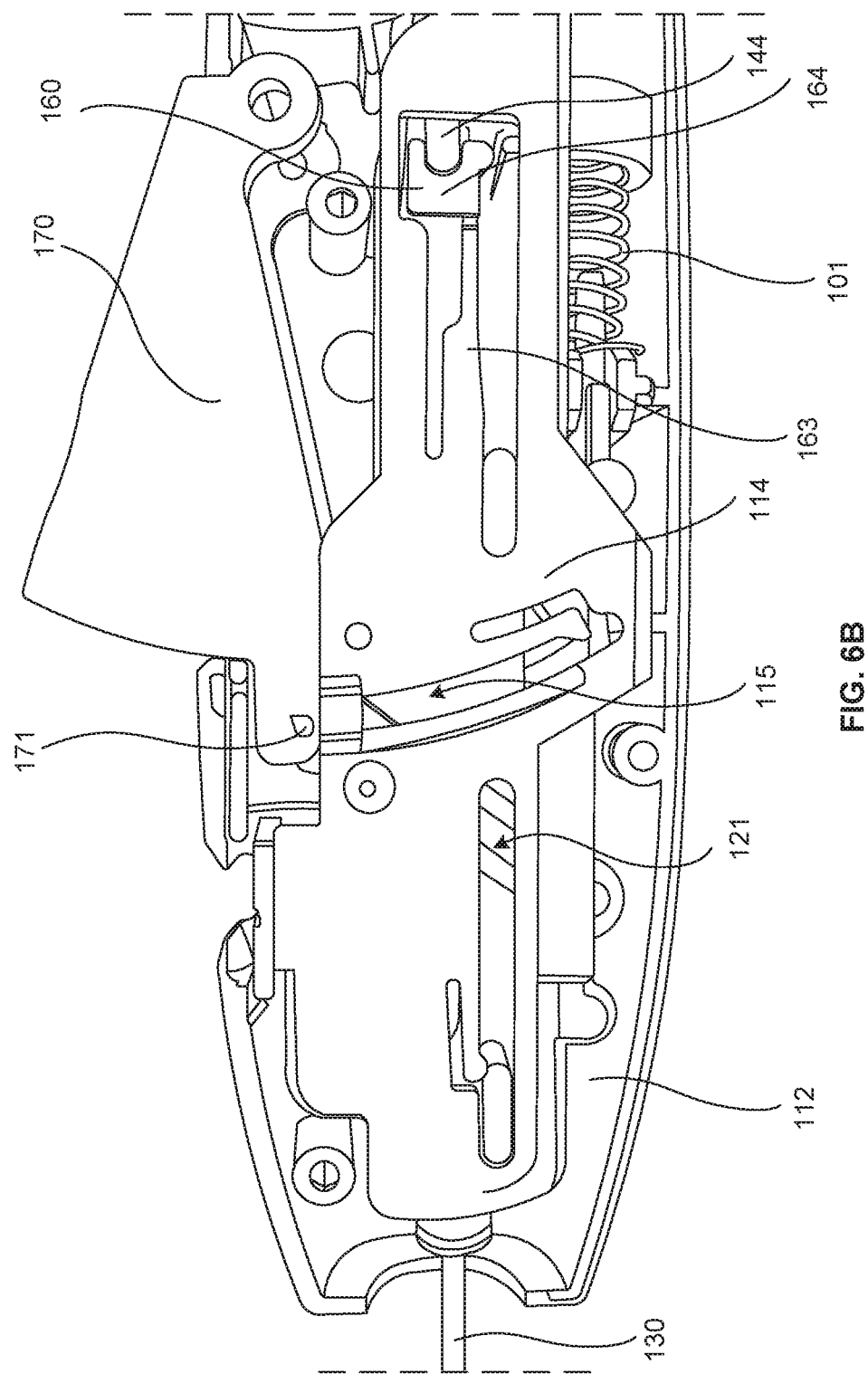
FIG. 6B is a side view of the device of FIG. 1 in a pre-deployment configuration (the sheath adapter and half of the outer housing are not shown).

When the deployment actuator 170 is in the unlocked position, shown in FIG. 6B, the deployment actuator 170 may be actuatable. The deployment actuator 170 may be moveable relative to the frame 114. More specifically, the actuator locking surface 171 may be positioned at an opening of, and may align with, the groove 115 in the frame 114 to allow actuation of the deployment actuator 170. The push rack actuating surface 173 of the deployment actuator 170 may be spaced from the actuating ramp 143 on the push rack. Compared to their respective positions when the deployment actuator 170 is in the locked position, the outer housing 112 and deployment actuator 170 may be positioned slightly proximally relative to the frame 114, pull rack 120, and push rack 140 when the deployment actuator 170 is in the unlocked position.

Figure 7A:
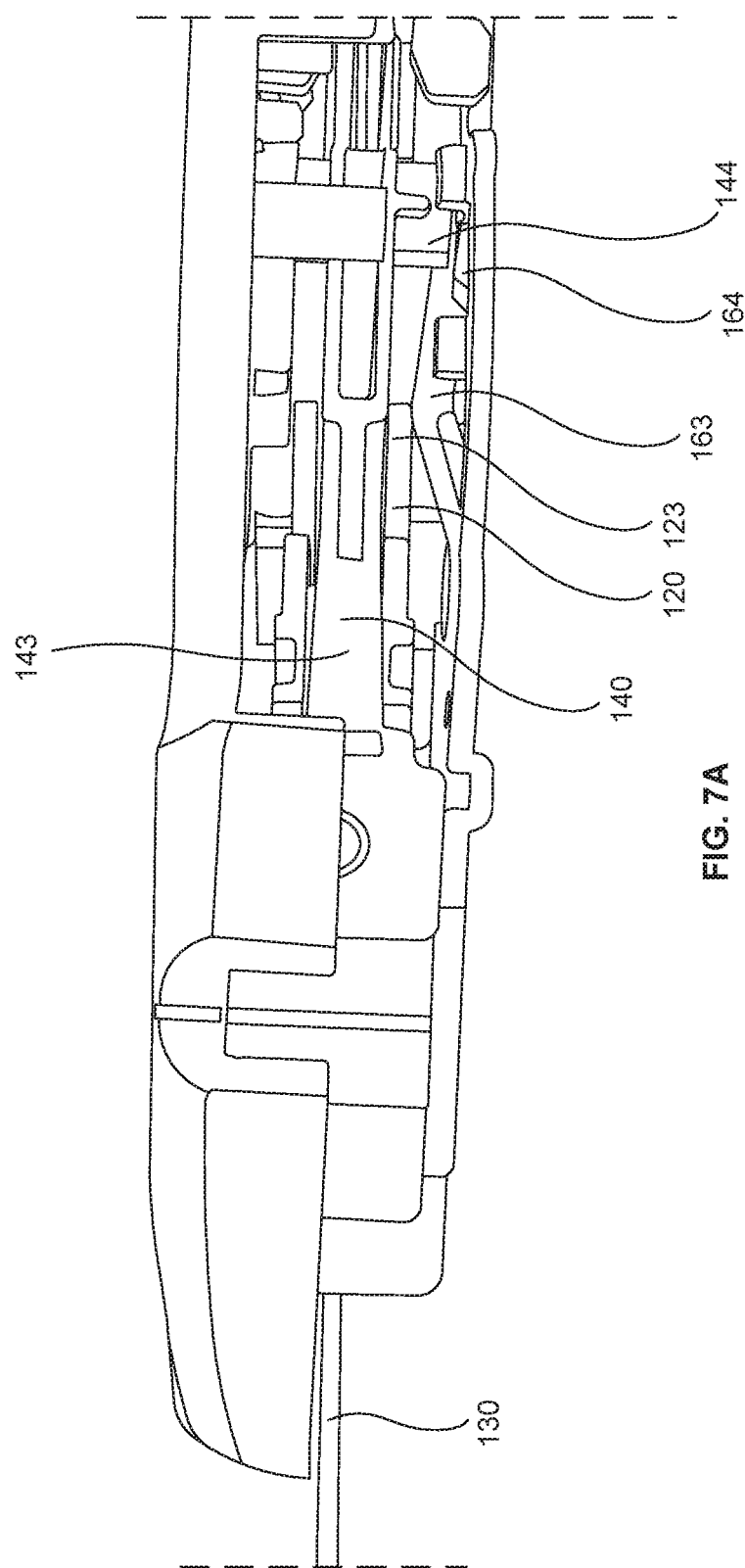
FIG. 7A is a top view of the device of FIG. 1 in a partially deployed configuration (the deployment actuator, sheath adapter, and half of the outer housing are not shown).
Figure 7B:
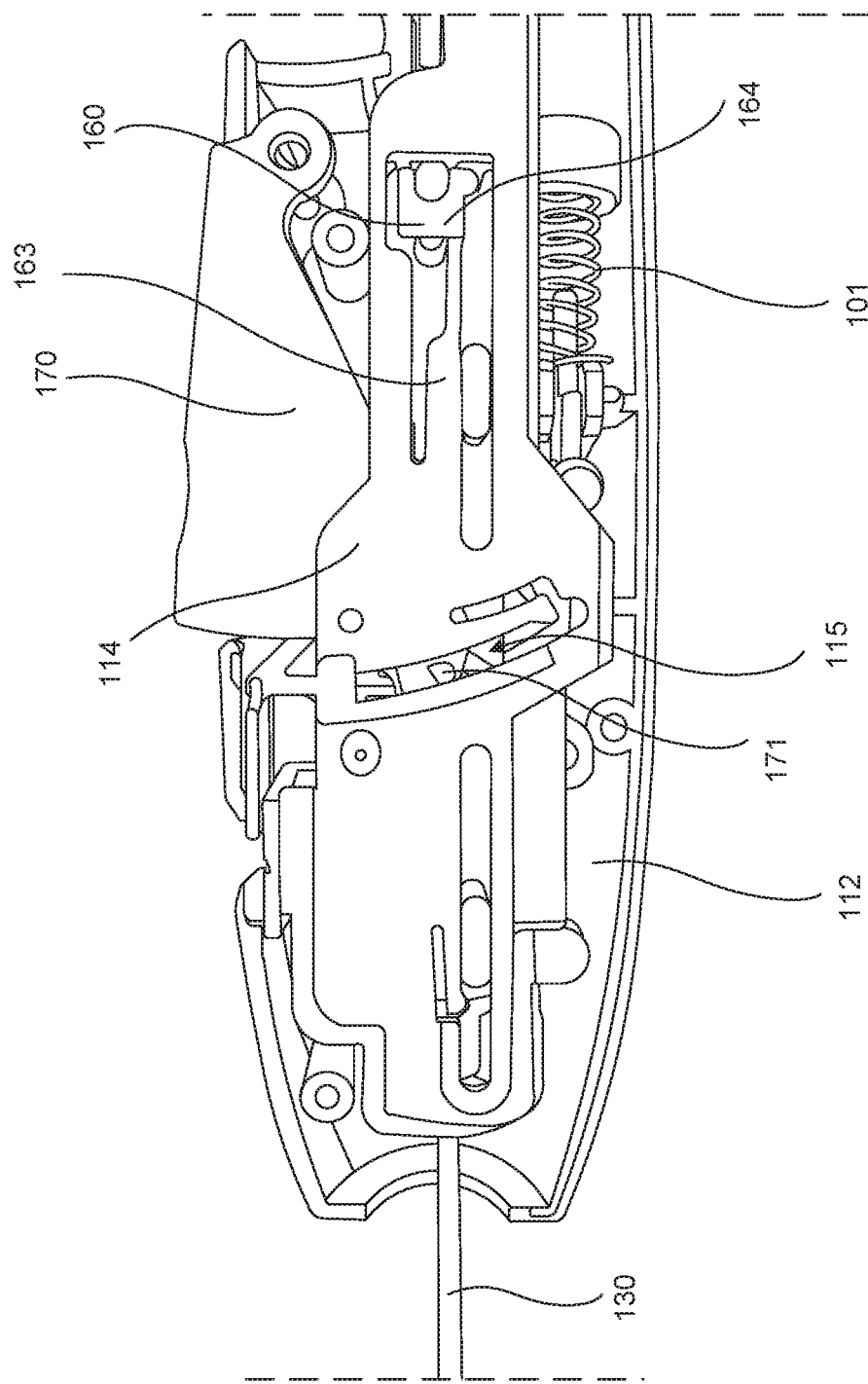
FIG. 7B is a side view of the device of FIG. 1 in a partially deployed configuration (the sheath adapter and half of the outer housing are not shown).

When the deployment actuator 170 is in the partially actuated position (also referred to as a partially depressed position), shown in FIG. 7B, the actuator locking surface 171 may be positioned in the groove 115 in the frame 114. The push rack actuating surface 173 of the deployment actuator 170 may be in contact with the actuating ramp 143 on the push rack 140. As the deployment actuator 170 is actuated, the actuator locking surface 171 may move along the groove 115 in the frame 114.

Figure 8A:
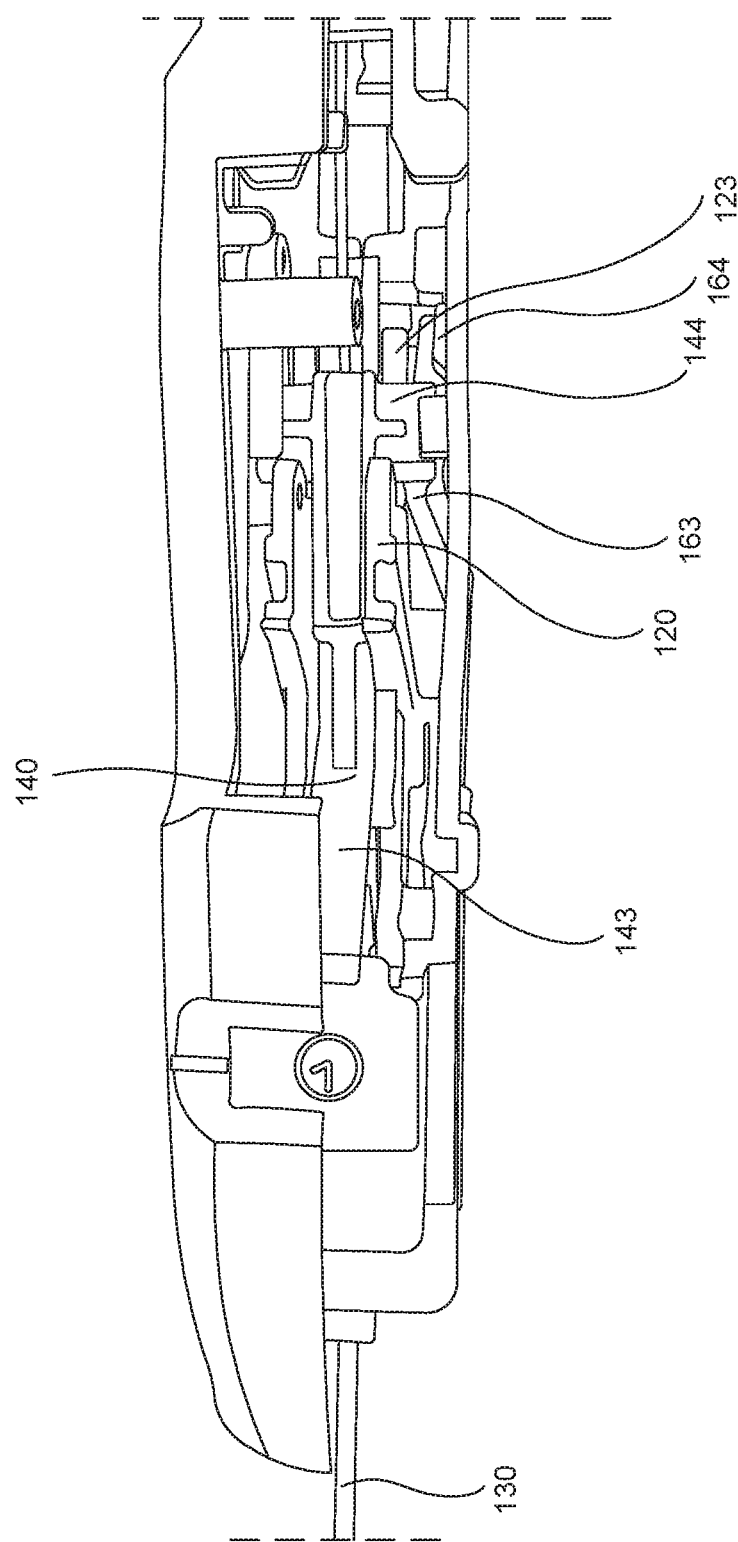
FIG. 8A is a top view of the device of FIG. 1 in a fully deployed configuration (the deployment actuator, sheath adapter, and half of the outer housing are not shown).
Figure 8B:
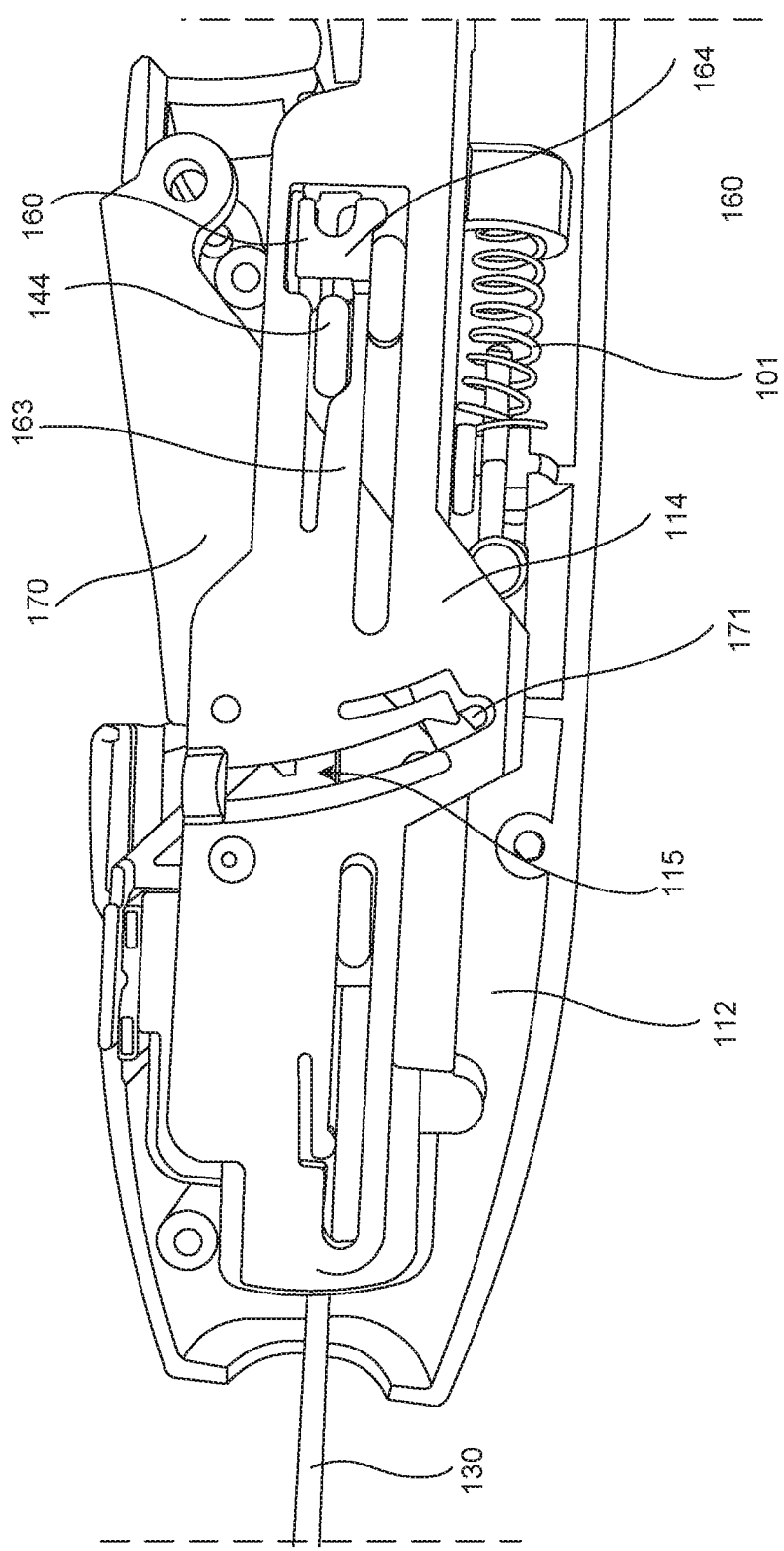
FIG. 8B is a side view of the device of FIG. 1 in a fully deployed configuration (the sheath adapter and half of the outer housing are not shown).

When the deployment actuator 170 is in the fully actuated position (also referred to as a fully depressed position), shown in FIG. 8B, the actuator locking surface 171 may be positioned in the groove 115 in the frame 114. When the deployment actuator 170 is in the fully actuated position, the actuator locking surface 171 may be positioned farther from the opening in the groove 115 in the frame 114 compared to its position when the deployment actuator 170 is in the partially actuated position. The push rack actuating surface 173 of the deployment actuator 170 may be in contact with the actuating ramp 143 on the push rack 140, and the push rack actuating surface 173 may be positioned farther down the ramp 143 on the push rack 140 compared to its position when the deployment actuator 170 is in the partially actuated position.

The device 100 may have a pull rack lock movable between a locked position and an unlocked position. In the locked position, the pull rack lock may engage the pull rack 120 to prevent proximal movement of the pull rack 120. In the unlocked position, the pull rack lock may be spaced from the pull rack 120, and the pull rack 120 and sealant sleeve 130 may be proximally movable relative to the outer housing 112, frame 114, and/or the pull rack lock to expose the sealant 2. The pull rack lock may be initially provided in the locked position. Moving the deployment actuator 170 from the locked position to the unlocked position may also move the pull rack lock from the locked position to the unlocked position. In the embodiment shown in FIG. 9, the pull rack actuating surface 172 on the deployment actuator 170 may also function as the pull rack lock because the pull rack actuating surface 172 contacts a proximal-facing surface of the pull rack 120 when the deployment actuator 170 is in the locked position, thereby preventing proximal movement of the pull rack.

The device 100 may have a push rack lock 160, shown in FIGS. 4A-4C, that is deflectable or otherwise movable between a locked position and an unlocked position. The push rack lock 160 may have a push rack engaging portion 164. In the locked position, shown in FIGS. 5A-5B, the push rack lock 160 may engage the push rack 140 to prevent distal movement of the push rack 140 and the support member 150. Specifically, the push rack engaging portion 164 of the push rack lock 160 may contact a latch-contacting surface 144 of the push rack 140. In the unlocked position, shown in FIGS. 7A-7B, the push rack lock 160 may be spaced from the push rack 140 such that the push rack 140 and the support member 150 are distally movable relative to the push rack lock 160.

The push rack lock 160 may be initially provided in the locked position to prevent advancement of the support member 150 in the event that distal forces are applied to the push rack 140 prematurely. For example, the push rack lock 160 may be in the locked position during shipping, handling, and preparation of the device 100 in advance of a procedure. The push rack lock 160 may also be in the locked position during the procedure until the sealant 2 is at least partially exposed in the puncture. The push rack lock 160 may be in the locked position when the deployment actuator 170 is in both the locked and unlocked positions. Moving the deployment actuator 170 from the unlocked position to the partially actuated position may also move the push rack lock 160 from the locked position to the unlocked position. The push rack lock 160 may be in the unlocked position when the deployment actuator 170 is in the partially actuated position.

When the push rack lock 160 is in the locked position, it may preferably remain in the locked position upon axial movement of the push rack 140 (or upon application of axial forces to the push rack 140). A push rack lock unlocking feature 123, shown in FIG. 2A, may be movable relative to the push rack 140 and the push rack lock 160 to move the push rack lock 160 from the locked position to the unlocked position. Axial (and preferably proximal) movement of the push rack lock unlocking feature 123 may cause lateral movement of a portion of the push rack lock 160. Lateral movement of a portion of the push rack lock 160 may unlock the push rack lock 160, thereby allowing axial (and preferably distal) movement of the push rack 140. In the embodiment shown in FIGS. 6A-7B, the push rack lock unlocking feature 123 is included on the pull rack 120 such that proximal movement of the pull rack 120 may unlock the push rack lock 160. When the push rack lock 160 is in the locked position, the pull rack 120 may be movable proximally relative to the push rack 140 and the push rack lock 160. When the push rack lock 160 is in the unlocked position, the pull rack 120 and the push rack 140 may both be axially movable relative to the push rack lock 160. Instead of being included on the pull rack 120, the push rack lock unlocking feature 123 may be included on another component, including the deployment actuator 170, outer housing 112, and/or frame 114. The push rack lock 160 may move from the locked position to the unlocked position upon actuation of the deployment actuator 170 and/or movement of the frame 114 relative to the outer housing 112. The device 100 may include a feature that prevents or limits premature movement of the push rack lock unlocking feature 123. For example, the pull rack 120 may have a pull rack lock provided in a locked position, the deployment actuator 170 may be provided in a locked position, and/or the spring 101 may limit movement of the frame 114 relative to the outer housing 112.

The push rack 140 and the support member 150 may be substantially unbiased in the axial direction, and more specifically, may be substantially unbiased relative to the sealant 2. Therefore, moving the push rack lock 160 from the locked position to the unlocked position does not automatically cause the push rack 140 to move distally toward the sealant 2. The push rack 140 may be able to maintain the same position before and after the push rack lock 160 is unlocked, until the deployment actuator 170 begins moving from a partially actuated position to a fully actuated position to advance the push rack 140. After the push rack lock 160 is moved from the locked position to the unlocked position, further movement of the deployment actuator 170 may move the push rack 140 distally.

The push rack lock 160 may be integrally formed with (or coupled to) various components of the device 100, including but not limited to the outer housing 112, the frame 114, the deployment actuator 170, or other components of the device 100. In one embodiment shown in FIG. 4A, the push rack lock 160 is integrally formed with the frame 114.

Figure 5A:
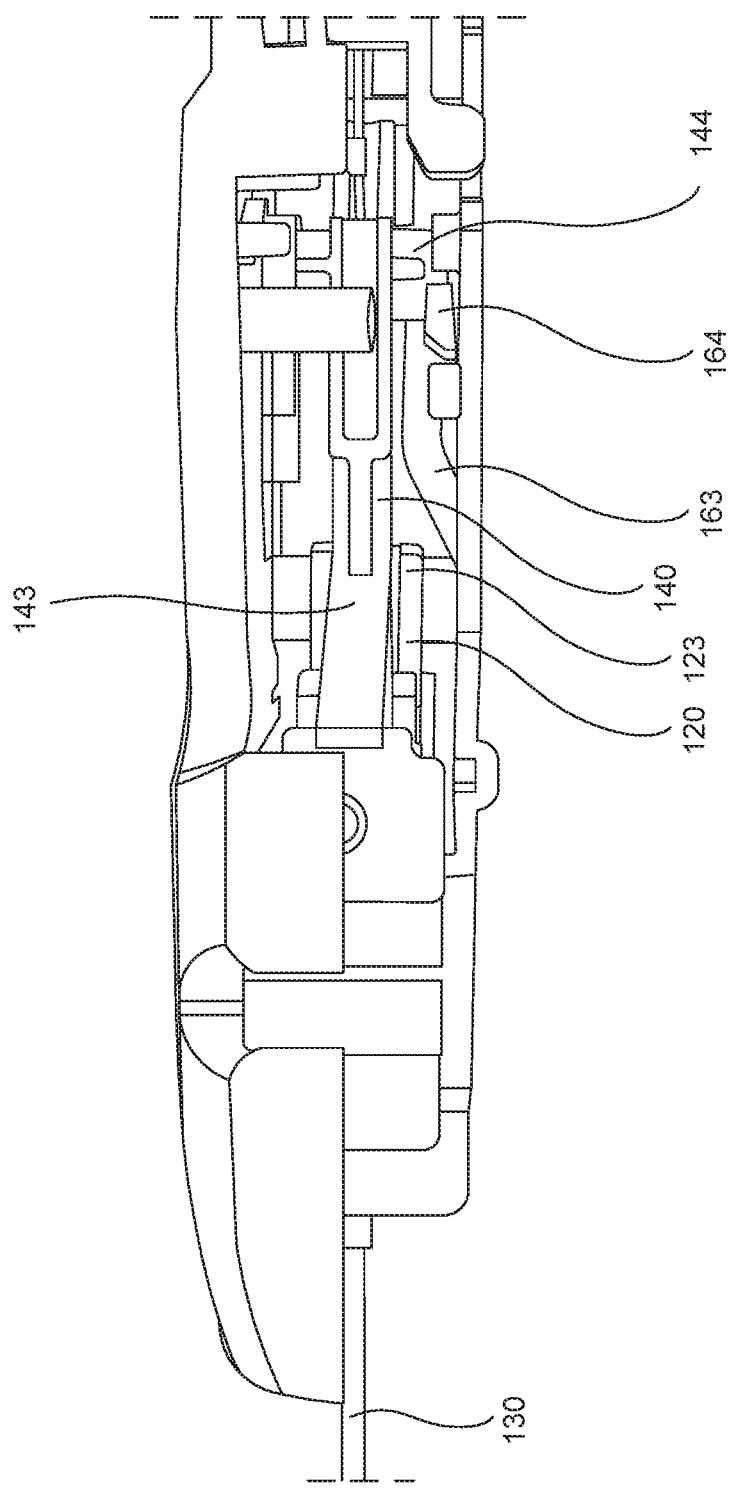
FIG. 5A is a top view of the device of FIG. 1 in a locating configuration (the deployment actuator, sheath adapter, and half of the outer housing are not shown).

In the embodiment shown in FIGS. 4A-4C, the push rack lock 160 may comprise a pull rack engaging portion 163 (shown as an arm 163 in FIGS. 4A-4C) and a push rack engaging portion 164 (shown as a latch 164 near one end of the arm 163 in FIGS. 4A-4C). The latch-contacting surface 144 on the push rack 140 may be a protrusion, as shown in FIG. 3. When the push rack lock 160 is in the locked position, as shown in FIGS. 5A-5B, the latch-contacting surface 144 of the push rack 140 may engage the latch 164 to prevent distal movement of the push rack 140. The push rack lock 160 may be deflected from the locked position to the unlocked position. When the push rack lock 160 is in the unlocked position, as shown in FIGS. 7A-7B, the latch-contacting surface 144 of the push rack 140 may be spaced or disengaged from the latch 164, allowing the push rack 140 to move distally relative to the latch 164. To unlock the push rack lock 160, the wall 123 on the pull rack 120 may slide along the arm 163 of the push rack lock 160, which may deflect the arm 163 and cause the latch 164 to move laterally and become spaced or disengaged from the latch-contacting surface 144 of the push rack 140. The latch 164 may contact at least a distal-facing surface of the latch-contacting surface 144 on the push rack 140. The latch 164 may also contact additional surfaces of the push rack 140. For example, the latch 164 may also contact a top-facing surface and/or a bottom-facing surface of the latch-contacting surface 144 on the push rack 140 to further limit movement of the latch 164 to a single direction, preferably a direction that is substantially perpendicular to the longitudinal axis 3 of the device 100 (also referred to as a radial direction or a lateral direction). In an exemplary embodiment shown in FIG. 5B, the latch 164 may comprise a u-shaped groove or slot having an opening at the proximal end of the slot such that movement of the latch 164 is limited to the radial direction when the latch 164 engages the latch-contacting surface 144.

During use, actuating the deployment actuator 170 may cause the pull rack 120 to move proximally and unlock the push rack lock 160. One benefit of the devices described herein is a gradual increase in the actuation force of the deployment actuator 170 while unlocking the push rack lock 160. The angle θ of the arm 163 of the push rack lock 160 (see FIG. 4B) may ensure a gradual increase in the actuation force. The angle θ of the arm 163 may be measured from a plane extending through the longitudinal axis 3, and may be less than about 60°. In another embodiment, the angle θ may be less than about 45°, less than about 40°, less than about 35°, less than about 30°, less than about 25°, or less than about 20°. In another aspect, the angle θ of the arm 163 may be between about 10° and about 60°, between about 20° and about 45°, between about 25° and about 40°, between about 30° and about 40°, or between about 32° and about 36°. In one embodiment, the angle θ of the arm 163 of the push rack lock 160 may be about 34°.

If the angle θ of the arm 163 is too high, the user may experience a sudden increase in the actuation force of the deployment actuator 170 as the pull rack 120 moves proximally and the push rack lock 160 moves to the unlocked position. However, if the angle θ of the arm 163 is too low, it may not provide enough resistance to prevent premature advancement of the push rack 140 if a proximal force is applied to the pull rack 120. Therefore, the device may include a feature that prevents or limits premature movement of the push rack lock unlocking feature 123 (as discussed above) to minimize the risk of prematurely unlocking the push rack lock 160 without creating an excessively high actuation force of the deployment actuator 170. For example, if the push rack lock unlocking feature 123 is provided on the pull rack 120, then the pull rack lock also limits or prevents premature movement of the push rack lock unlocking feature 123. The actuation force of the deployment actuator 170 may be between about 5N and about 40N. In another aspect, the actuation force may be between about 10 N and about 30 N, or between about 15 N and about 20 N.

Figure 5C:
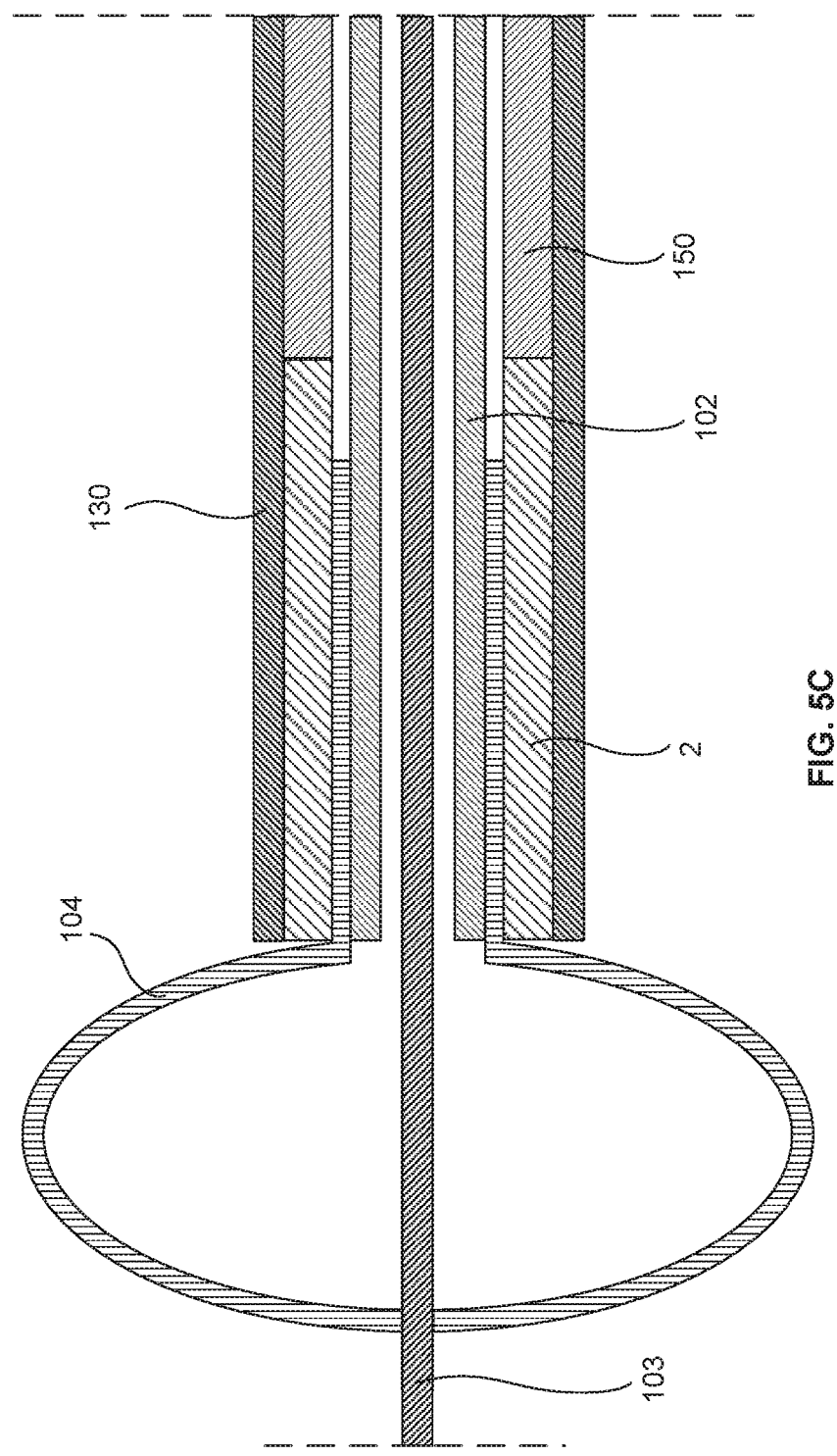
FIG. 5C is a cross-sectional view of the distal section of the device of FIG. 1 in a locating configuration.

The device 100 may also have a feature to position the sealant 2 in the puncture. For example, the device 100 may include an elongate member 102 coupled to the frame 114. The elongate member 102, shown in FIG. 5C, may extend along the longitudinal axis 3 of the device 100 shown in FIG. 1. The elongate member 102 may extend through the lumen 153 of the support member 150 and a lumen of the sealant 2. A radially-expandable positioning element 104 (including but not limited to a balloon, wire mesh, or foot plate, for example) may be provided on a distal section of the elongate member 102. The proximal end of the positioning element 104 may be connected to the elongate member 102, and the distal end of the positioning element 104 may be connected to a core wire 103, as shown in FIG. 5C. The core wire 103 may extend along the longitudinal axis 3 of the device 100, in a lumen of the elongate member 102, and may move axially as the positioning element 104 moves between the radially-expanded configuration and the radially-contracted configuration. The positioning element 104 may be inserted into the vessel in a radially-contracted configuration. When the positioning element 104 is in the vessel, it may be moved to a radially-expanded configuration and the device 100 may be withdrawn proximally until the positioning element 104 contacts the vessel wall, which may provide tactile confirmation that the device has been positioned properly. If the positioning element 104 is a balloon, the balloon may be moved to the radially-expanded configuration by inflating the balloon. Moving the positioning element 104 to the radially-expanded configuration may also move the core wire 103 proximally relative to the elongate member 102. Once the positioning element 104 contacts the vessel wall, continuing to apply a proximal force to the outer housing 112 may compress the spring 101, move the outer housing 112 (and the deployment actuator 170) proximally relative to the frame 114, and apply tension to the frame 114 and/or elongate member 102. Moving the deployment actuator 170 relative to the frame 114 may move the deployment actuator 170 to the unlocked position, thereby allowing deployment of the sealant 2. After the sealant 2 is deployed, the positioning element 104 may be moved to the radially-contracted configuration and the device 100 may be withdrawn from the puncture. If the positioning element 104 is a balloon, the balloon may be moved to the radially-contracted configuration by deflating the balloon.

Figure 10:
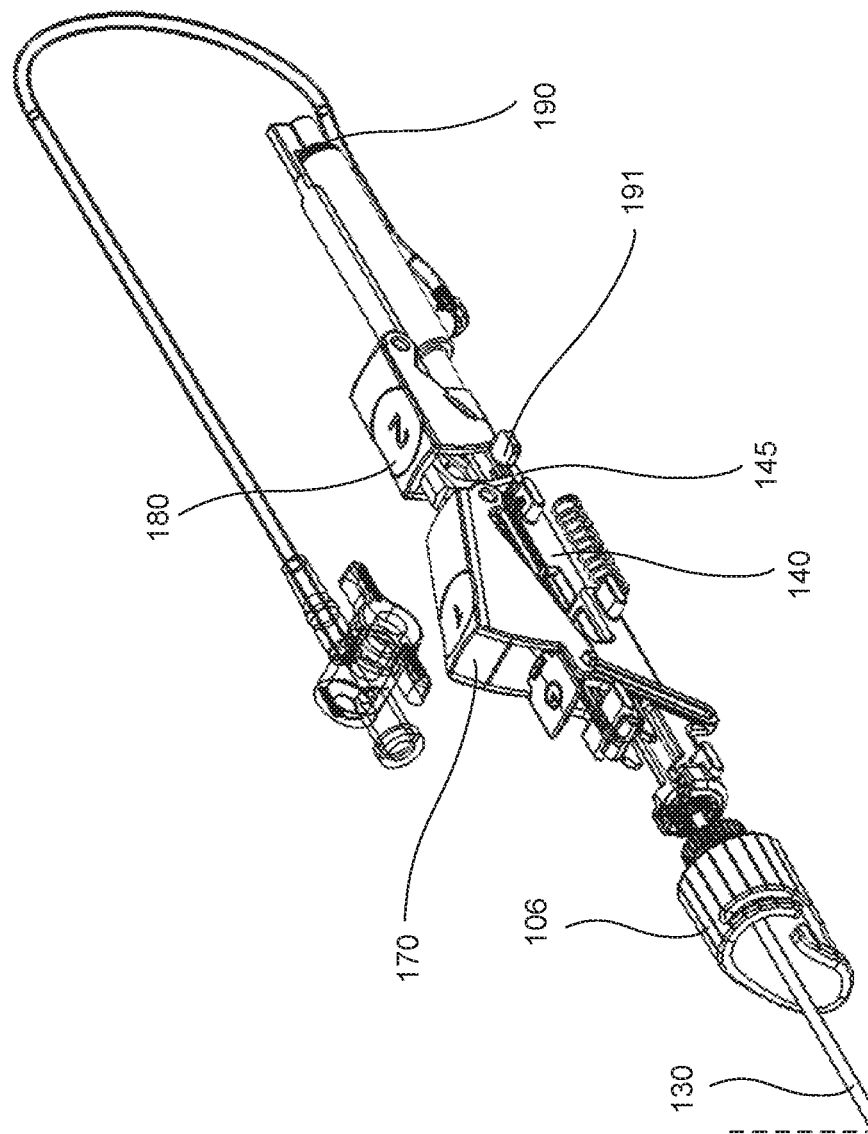
FIG. 10 is a perspective view of the device of FIG. 1 (the outer housing and frame are not shown).

The device 100 may also include a positioning element indicator 190, shown in FIG. 10. The positioning element indicator 190 may have a first position that provides a visual indication that the positioning element 104 is in a radially-contracted configuration. The positioning element indicator 190 may have a second position that provides a visual indication that the positioning element 104 is in a radially-expanded configuration. The positioning element indicator 190 may be coupled to the core wire 103, such that axial movement of the core wire 103 also moves the positioning element indicator 190 axially between the first and second positions.

Figure 5D:
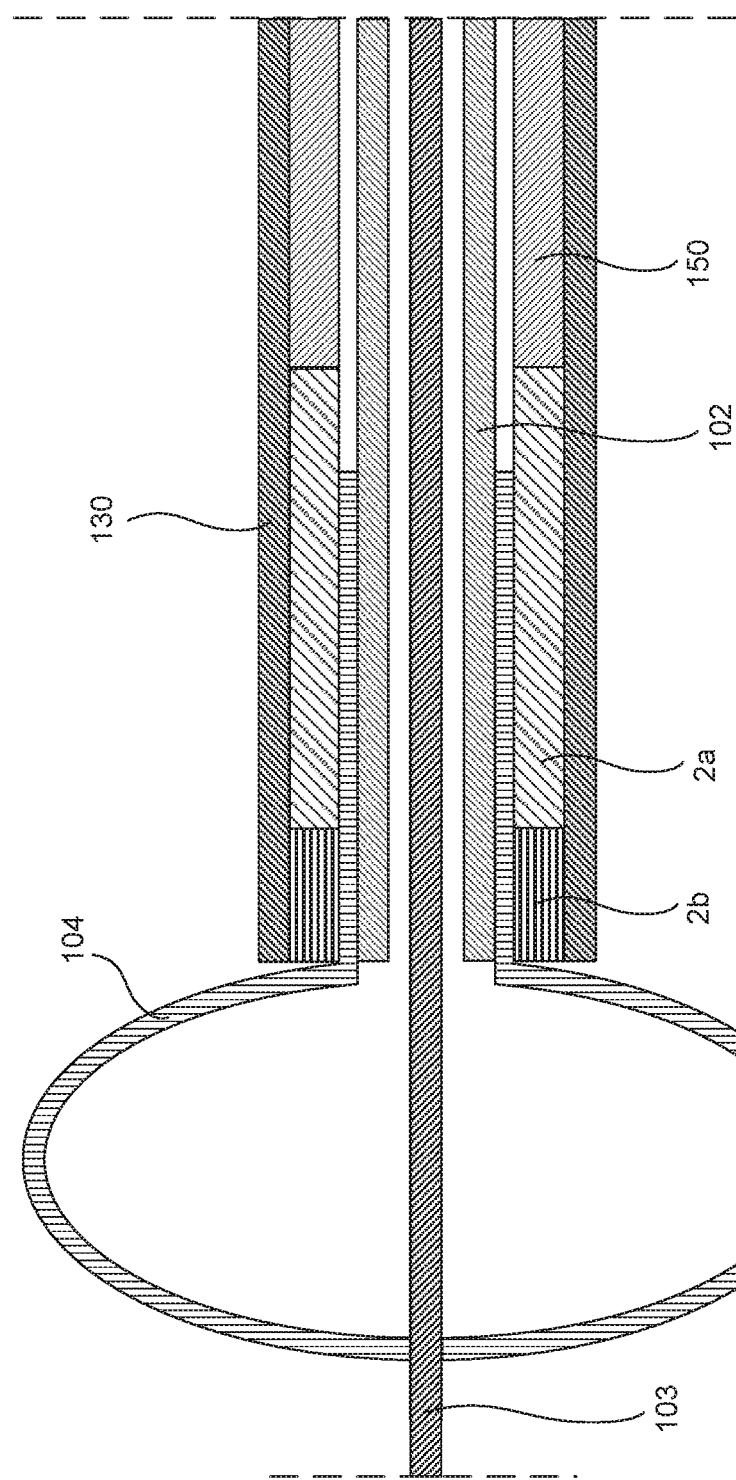
FIG. 5D is a cross-sectional view of the distal section of the device of FIG. 1 in a locating configuration, showing an embodiment of a sealant having a proximal section and a distal section.

An exemplary embodiment of the sealant 2 is shown in FIGS. 5C, 6C, 7C, and 8C, and may comprise known materials used for sealing punctures, including but not limited to collagen, freeze-dried hydrogels, non-cross-linked hydrogel precursors, chitosan, and combinations thereof. A lumen may extend through the sealant 2. The sealant 2 may be positioned in the distal section 132 of the sealant sleeve 130, radially between the elongate member 102 and the sealant sleeve 130. For example, the elongate member 102 may extend through the lumen of the sealant 2, and the sealant sleeve 130 may surround the sealant 2. The support member 150 may be proximal to the sealant 2, such that a distal surface of the support member 150 may contact the sealant 2. FIG. 5D shows the same device having an alternative embodiment of a sealant. The sealant of FIG. 5D may include a proximal section 2a formed from freeze-dried hydrogel, and a distal section 2b formed from a plurality of non-freeze-dried and/or non-cross-linked precursors. The distal section 2b may face or contact the positioning element 104.

FIGS. 5A-8C show an exemplary method for deploying the sealant 2 in a puncture. The device 100 may be provided in a resting configuration. The device 100 is not shown in the resting configuration in FIGS. 5A-8C; however, the resting configuration is similar to the locating configuration shown in FIGS. 5A-5C, except the positioning element 104 may be in a radially-contracted configuration when the device is in the resting configuration. The deployment actuator 170, pull rack lock and/or push rack lock 160 may be in their respective locked positions. The pull rack actuating surface 172, shown in FIG. 9, may function as a pull rack lock, and may contact a stop 122 on the pull rack 120 shown in FIG. 2A and/or may be offset from the opening 125 in the groove 121 in the pull rack 120 to prevent proximal movement of the pull rack 120. The push rack lock 160 may engage the push rack 140 to prevent distal movement of the push rack 140. The push rack 140 may be spaced or disengaged from the deployment actuator 170. When the device 100 is in the resting configuration, the positioning element indicator 190 may be in the first position, indicating that the positioning element 104 is in a radially-contracted configuration.

The distal end of the device 100 may be inserted into the puncture while the device 100 is in the resting configuration. When the positioning element 104 is in the vessel, the positioning element 104 may be moved to the radially-expanded configuration, bringing the device to a locating configuration, shown in FIGS. 5A-5C. The positioning element indicator 190 may move to the second position, indicating that positioning element 104 is in the radially-expanded configuration. The device 100 may be withdrawn proximally until the expanded positioning element 104 contacts the vessel wall.

Once the positioning element 104 contacts the vessel wall, continuing to withdraw the device 100 may move the device 100 from the locating configuration to a pre-deployment configuration. In the embodiment shown in FIGS. 5B and 6B, continuing to withdraw the outer housing 112 may move the device 100 from the locating configuration to the pre-deployment configuration by compressing the spring 101 and applying tension to the frame 114 and/or elongate member 102. Tension may be applied when the vessel wall applies a distal force to the frame 114 and elongate member 102 (via the positioning element 104) while the spring 101 applies a proximal force to the frame 114 and elongate member 102. The deployment actuator 170 and/or the pull rack lock may move from their respective locked positions to their respective unlocked positions. The push rack lock 160 may remain in the locked position. The deployment actuator 170 (together with the outer housing 112) may move proximally relative to the frame 114, pull rack 120, and push rack 140. The device 100 may include a tension indicator, which can indicate that an appropriate amount of tension is being applied to the frame 114, and also indicate that the device 100 is in the pre-deployment configuration. An exemplary tension indicator 105, shown in FIG. 1, may comprise a marking on the frame 114 that aligns with markings adjacent a window in the outer housing 112 to indicate that the frame 114 is under tension, however any other appropriate tension indicator can be used that provides a similar function. Therefore, the device 100 in FIG. 1 is in the pre-deployment configuration because the frame 114 and/or elongate member 102 is under tension and the deployment actuator 170 has not been actuated.

Figure 6C:
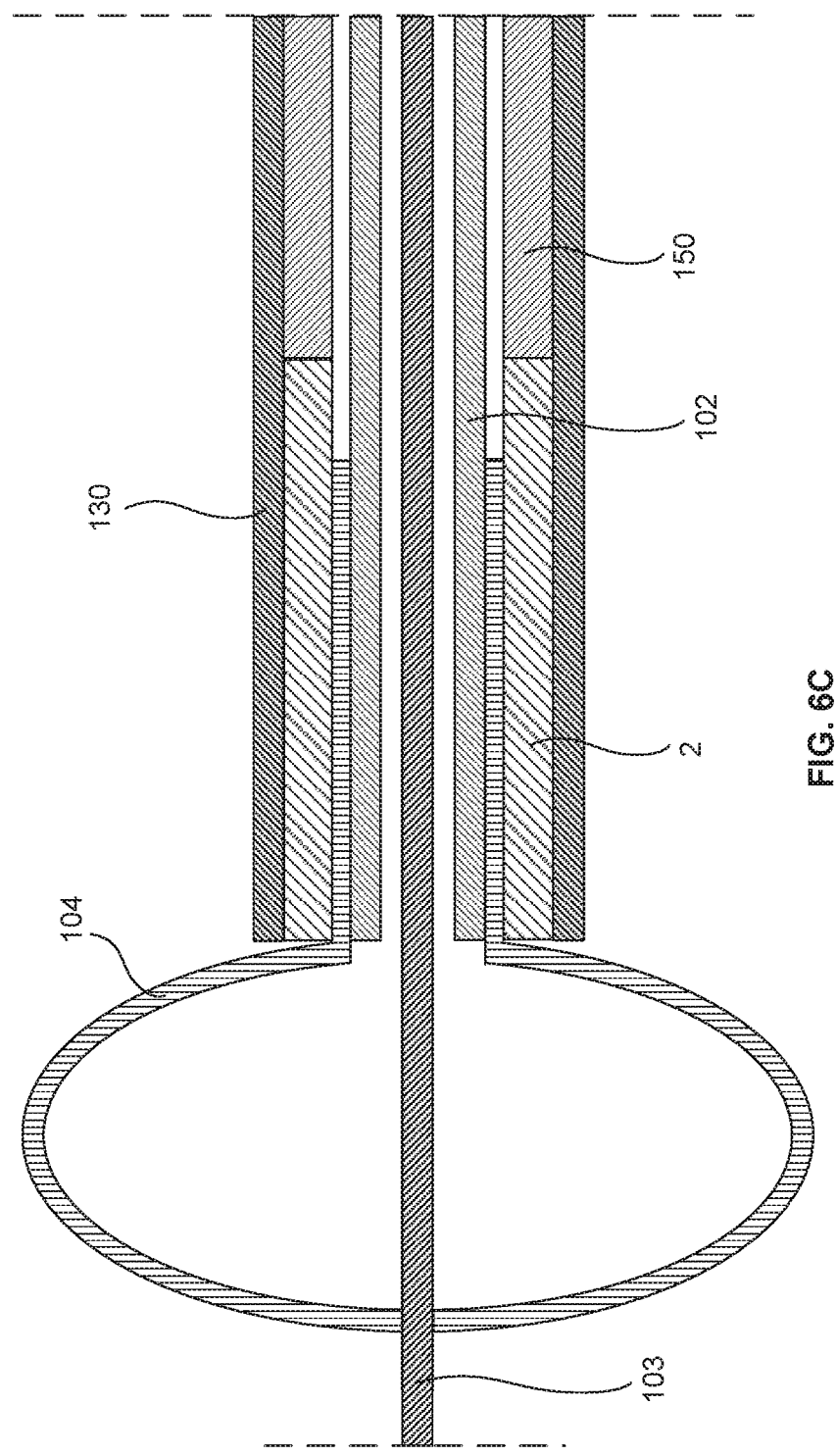
FIG. 6C is a cross-sectional view of the distal section of the device of FIG. 1 in a pre-deployment configuration.

When the device 100 is in the pre-deployment configuration, shown in FIGS. 6A-6C, the deployment actuator 170 and/or the pull rack lock may be in their respective unlocked positions. The push rack lock 160 may be in the locked position. The pull rack actuating surface 172 of the deployment actuator 170 may align with an opening 125 in a groove 121 in the pull rack 120, allowing for proximal movement of the pull rack 120. The push rack 140 may be spaced from the deployment actuator 170. Compared to their respective positions when the device is in the resting and locating configurations, the outer housing 112 and deployment actuator 170 may be positioned slightly proximally relative to the frame 114, pull rack 120, and push rack 140 when the device is in the pre-deployment configuration. The position of the frame 114, pull rack 120, and push rack 140 relative to one another may be substantially the same when the device 100 is in the resting, locating, and pre-deployment configurations.

The device 100 may be moved from the pre-deployment configuration to the partially deployed configuration, preferably by moving the deployment actuator 170 from the unlocked position to the partially actuated position. Moving the device 100 from the pre-deployment configuration to the partially deployed configuration may move the pull rack 120 and the sealant sleeve 130 proximally to expose at least a portion of the sealant 2. The pull rack actuating surface 172 may move into and slide along at least part of the groove 121 in the pull rack 120. Moving the device 100 from the pre-deployment configuration to the partially deployed configuration may move the push rack actuating surface 173 of the deployment actuator 170 toward the push rack 140, and may move the push rack lock 160 from the locked position to an unlocked position. The push rack 140 and the support member 150 may remain substantially stationary relative to the push rack lock 160 when the device 100 is moved from the pre-deployment configuration to the partially deployed configuration. A distal surface of the support member 150 may contact the sealant 2, such that the support member 150 prevents proximal movement of the sealant 2 and maintains the position of the sealant 2 as the sealant sleeve 130 is retracted, thereby exposing the sealant 2.

Figure 7C:
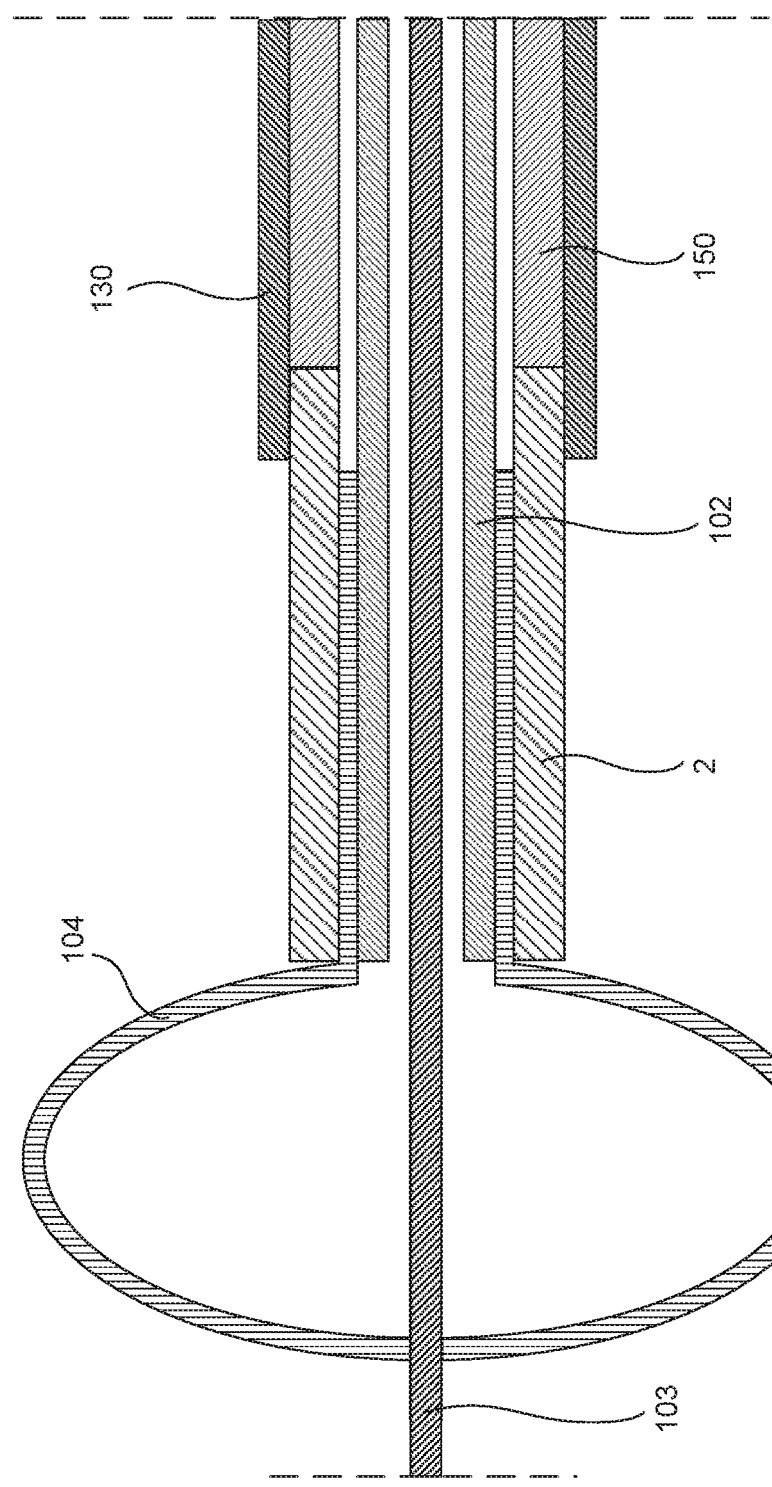
FIG. 7C is a cross-sectional view of the distal section of the device of FIG. 1 in a partially deployed configuration.

When the device 100 is in the partially deployed configuration, shown in FIGS. 7A-7C, the sealant sleeve 130 may be at least partially retracted and the sealant 2 may be at least partially exposed. The deployment actuator 170 may be in the partially actuated position. The pull rack actuating surface 172 may be positioned in the groove 121 in the pull rack 120. The pull rack 120 may be positioned proximally compared to its position when the device 100 is in the pre-deployment configuration, such that the pull rack 120 and sealant sleeve 130 are at least partially retracted. The push rack lock 160 may be in an unlocked position, such that the push rack lock 160 is spaced from the push rack 140. The deployment actuator 170 may now engage the push rack 140, although the position axial position of push rack 140 relative to the frame 114 and/or push rack lock 160 may be substantially the same when the device 100 is in the pre-deployment configuration and the partially deployed configuration. Specifically, the push rack actuating surface 173 of the deployment actuator 170 may contact the actuating ramp 143 on the push rack 140.

The device 100 may then be moved from the partially deployed configuration to the fully deployed configuration, preferably by moving the deployment actuator 170 from the partially actuated position to the fully actuated position. The push rack 140 may move distally and the support member 150 may move to a fully advanced position. Specifically, the push rack actuating surface 173 of the deployment actuator 170 may slide along the actuating ramp 143 and move the push rack 140 distally. The pull rack 120 and sealant sleeve 130 may move proximally to the fully retracted position, or they may remain in the fully retracted position if they were fully retracted in the partially deployed configuration.

Figure 8C:
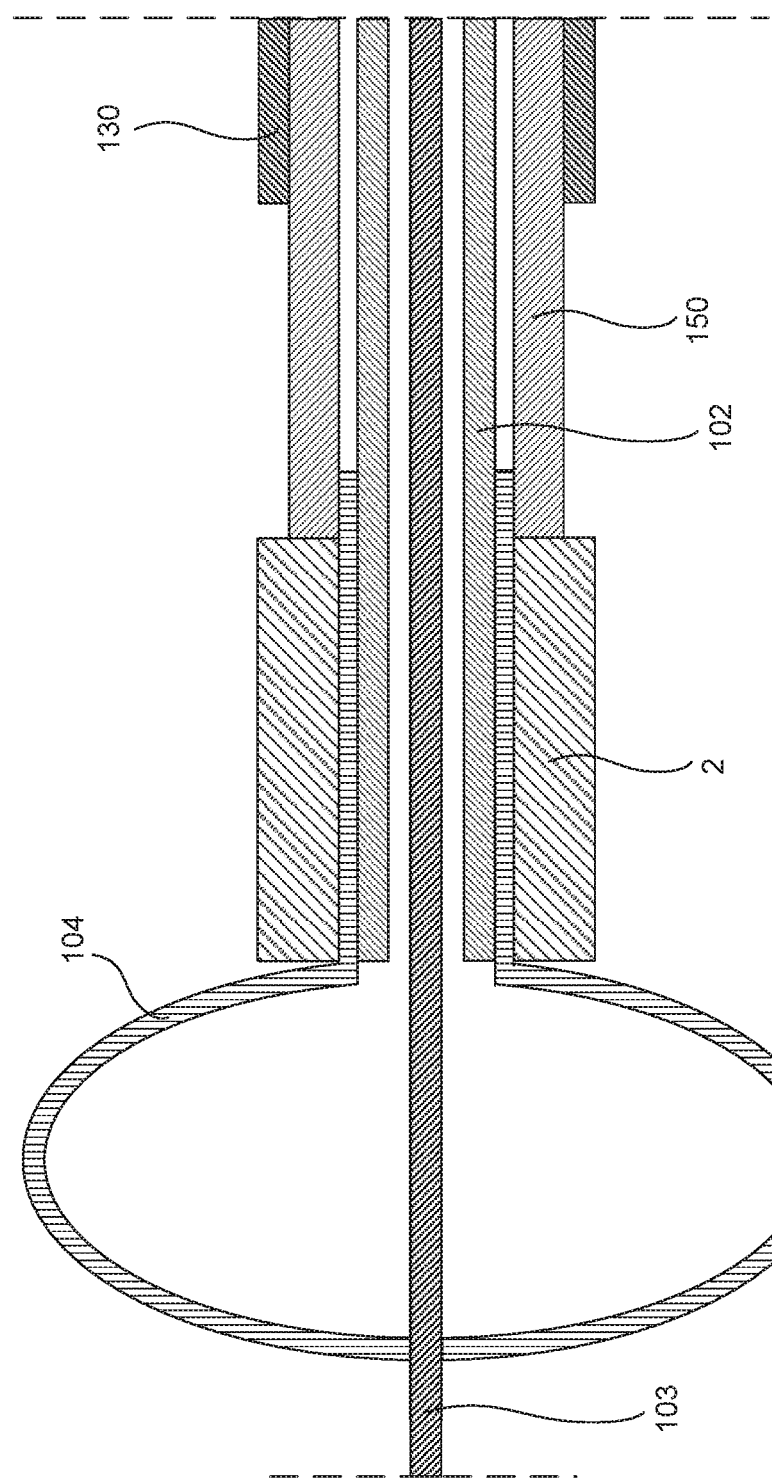
FIG. 8C is a cross-sectional view of the distal section of the device of FIG. 1 in a fully deployed configuration.

When the device 100 is in the fully deployed configuration, shown in FIG. 8A-8C, the sealant 2 may be exposed and compressed (or tamped) in the puncture. The deployment actuator 170 may be in a fully actuated position. The pull rack 120 may be positioned either in the same position or proximal to its position when the device 100 is in a partially deployed configuration, such that the pull rack 120 and sealant sleeve 130 are retracted from the sealant 2 and the sealant 2 is exposed in the puncture. The push rack 140 may be moved distally relative to the frame 114 and/or push rack lock 160 compared to their respective positions when the device 100 is in the partially deployed configuration, such that the push rack 140 and support member 150 are advanced toward the sealant 2 and the sealant 2 is tamped.

After the sealant 2 is exposed and compressed, the device 100 may be withdrawn from the puncture. The retraction actuator 180, shown in FIGS. 1 and 10, may be actuated to retract the positioning element 104, elongate member 102, and core wire 103 relative to the support member 150, such that the positioning element 104 may be withdrawn through the sealant 2 while the support member 150 prevents the sealant 2 from moving proximally. The retraction actuator 180 may cause the elongate member 102 and core wire 103 to slide proximally. Alternatively, the retraction actuator 180 may bend or kink the elongate member 102 and core wire 103, causing the distal ends of the elongate member 102 and core wire 103 to move proximally.

One or more lockout mechanisms may prevent the user from prematurely depressing the retraction actuator 180. First, the push rack 140 may include a first retraction actuator locking surface 145, shown in FIG. 10, that prevents the retraction actuator 180 from being actuated before the sealant 2 has been tamped. When the device 100 is in the resting, locating, pre-deployment, and partially deployed configurations, the first retraction actuator locking surface 145 may contact the retraction actuator 180 to prevent actuation of the retraction actuator 180. When the push rack 140 moves distally and the device 100 is in the fully deployed configuration, the first retraction actuator locking surface 145 may be spaced from the retraction actuator 180 to allow actuation of the retraction actuator 180. Second, the positioning element indicator 190 may include a second retraction actuator locking surface 191, also shown in FIG. 10. When the positioning element indicator 190 is in the second position and the positioning element 104 is in the radially-expanded configuration, the second retraction actuator locking surface 191 may contact the retraction actuator 180 to prevent actuation of the retraction actuator 180. When the positioning element indicator 190 is in the first position and the positioning element 104 is in the radially-contracted configuration, the second retraction actuator locking surface 191 may be spaced from the retraction actuator 180 to allow actuation of the retraction actuator 180. Therefore, the retraction actuator 180 may be actuated after the sealant 2 has been tamped and the positioning element 104 has been returned to the radially-contracted configuration. Once the retraction actuator 180 has been actuated and the positioning element 104 has been retracted through the sealant 2, the device 100 may be withdrawn from the puncture.

As used herein, the relative terms "proximal" and "distal" shall be defined from the perspective of the closure system. Thus, proximal refers to the direction of the handle of the closure system and distal refers to the direction of the distal tip of the closure system. The term "axial" refers to a direction parallel to the longitudinal axis of the device. The terms "radial" and "lateral" refer to a direction lying in a plane perpendicular to the longitudinal axis of the device. The terms "retracting" and "withdrawing" indicate proximal movement, and the term "advancing" indicates distal movement.

Any methods disclosed herein need not be performed in the order recited. The methods disclosed herein include certain actions taken by a practitioner; however, they can also include any third-party instruction of those actions, either expressly or by implication. For example, actions such as "tamping the sealant" include "instructing tamping of the sealant."

Although certain embodiments and examples have been described herein, it will be understood by those skilled in the art that many aspects of the closure system shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A system for closing a puncture, the system comprising:
a housing;
a frame positioned within the housing and axially movable within the housing;
a sealant sleeve movable with the frame;
a support member positioned within a lumen of the sealant sleeve and movable with the frame;
a sealant positioned in a distal end of the sealant sleeve, and wherein a distal end of the support member is positioned adjacent a proximal end of the sealant; and
a deployment actuator coupled to the housing and actuatable to actuate the sealant sleeve in a first direction, and actuating the support member in a second direction opposite the first direction;
wherein the frame is movable between a first position in which the frame prevents actuation of the deployment actuator and a second position in which the frame allows actuation of the deployment actuator.

2. The system of claim 1, wherein the frame is biased proximally relative to the housing.

3. The system of claim 1, wherein the frame includes an elongate member having a positioning element at a distal end thereof, and wherein the frame moves to the second position upon application of tension to the elongate member.

4. The system of claim 1, wherein a distal end of the sealant sleeve is coupled to a first rack member selectively engagable with the frame and the deployment actuator, and wherein a distal end of the deployment actuator includes an actuation feature configured to engage a corresponding actuation feature of the first rack member when the frame is in the second position.

5. The system of claim 4, wherein the actuation feature of the deployment actuator is configured to actuate the corresponding actuation feature of the first rack member to retract the sealant sleeve.

6. The system of claim 5, wherein the actuation feature of the deployment actuator includes a protrusion and the corresponding actuation feature of the first rack member is a groove.

7. The system of claim 5, wherein the actuation feature of the deployment actuator is a first actuation feature positioned on a first surface of the deployment actuator, and wherein the deployment actuator includes a second actuation feature configured to engage a corresponding actuation feature on the frame.

8. The system of claim 7, wherein the actuation feature of the first rack member is a groove angled toward a distal end of the housing and wherein the actuation feature of the frame is a groove angled toward a proximal end of the housing.

9. The system of claim 1, wherein a proximal end of the support member is coupled to a second rack member selectively engagable with the frame and the deployment actuator, and wherein a distal end of the deployment actuator includes an actuation feature configured to engage a corresponding actuation feature of the second rack member to extend the second rack member, thereby causing the support member to tamp the sealant.

10. The system of claim 9, wherein the actuation feature of the deployment actuator includes a wall and wherein the actuation feature of the second rack member includes a ramp.

11. The system of claim 1, wherein actuating the sealant sleeve in the first direction retracts the sealant sleeve, thereby exposing at least a portion of the sealant, and actuating the support member in the second direction causes the support member to tamp the sealant.

\* \* \* \* \*